(12) United States Patent
Chan et al.

(10) Patent No.: US 6,998,363 B2
(45) Date of Patent: Feb. 14, 2006

(54) POLYOLEFIN CATALYST COMPONENT USING NON-COVALENT INTERACTIONS

(75) Inventors: Michael Chi-Wang Chan, Hong Kong (CN); Chi-Fai Kui, Hong Kong (CN)

(73) Assignee: The University of Hong Kong, (HK)

( * ) Notice: Subject to any disclaimer, the term of this patent is extended or adjusted under 35 U.S.C. 154(b) by 204 days.

(21) Appl. No.: 10/643,858

(22) Filed: Aug. 19, 2003

(65) Prior Publication Data

US 2004/0248728 A1 Dec. 9, 2004

Related U.S. Application Data

(60) Provisional application No. 60/404,452, filed on Aug. 19, 2002.

(51) Int. Cl.
*B01J 31/00* (2006.01)
*B01J 37/00* (2006.01)
*C08F 4/02* (2006.01)
*C08F 4/60* (2006.01)
*C08F 4/44* (2006.01)

(52) U.S. Cl. ........................ 502/103; 502/117; 502/153; 502/154; 502/155; 526/133; 526/134; 526/160; 526/161; 526/172

(58) Field of Classification Search ................ 502/102, 502/103, 117, 153, 154, 155; 526/133, 134, 526/160, 161, 172
See application file for complete search history.

(56) References Cited

U.S. PATENT DOCUMENTS

| | | | |
|---|---|---|---|
| 6,825,296 B2 * | 11/2004 | Chi-Wang Chan et al. | 526/161 |
| 6,878,662 B2 * | 4/2005 | Murray | 502/155 |
| 2003/0191015 A1 * | 10/2003 | Chi-Wang Chan et al. | 502/150 |

\* cited by examiner

Primary Examiner—J. A. Lorengo
Assistant Examiner—J. Pasterczyk
(74) Attorney, Agent, or Firm—Dickstein, Shapiro, Morin & Oshinsky, LLP.

(57) ABSTRACT

An olefin polymerization catalyst system is prepared from a catalyst of formula I or II:

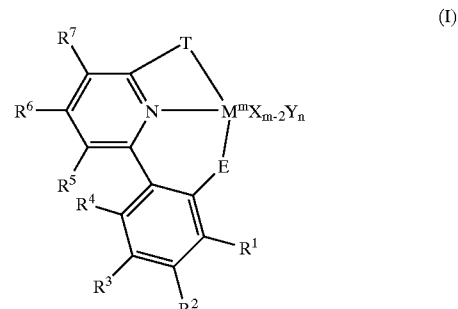

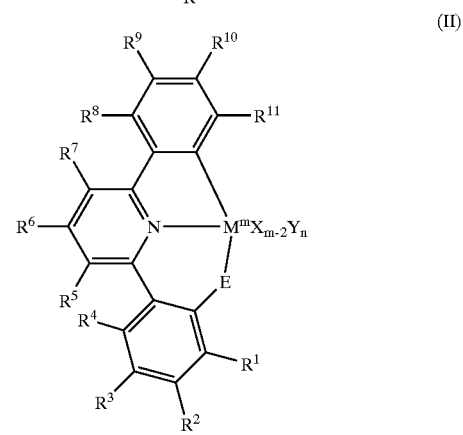

$R^1$–$R^7$ and $R^1$–$R^{12}$ in formulae I and II, respectively, are each independently —H, -halo, —$NO_2$, —CN, —($C_1$–$C_{30}$)

hydrocarbyl, —O($C_1$–$C_{30}$)hydrocarbyl, —N(($C_1$–$C_{30}$)hydrocarbyl)$_2$, —Si(($C_1$–$C_{30}$)hydrocarbyl)$_3$, —($C_1$–$C_{30}$)heterohydrocarbyl, -aryl, or -heteroaryl, each being unsubstituted or substituted with one or more —$R^8$ and —$R^{12}$ groups, respectively. Two $R^1$–$R^7$ can be joined to form a cyclic group. $R^8$ in formula I is -halo, —($C_1$–$C_{30}$)hydrocarbyl, —O($C_1$–$C_{30}$)hydrocarbyl, —$NO_2$, —CN, —Si(($C_1$–$C_{30}$)hydrocarbyl)$_3$, —N(($C_1$–$C_{30}$)hydrocarbyl)$_2$, —($C_1$–$C_{30}$)heterohydrocarbyl, -aryl, or -heteroaryl. T in formula I is —$CR^9R^{10}$— wherein $R^9$ and $R^{10}$ are defined as for $R^1$ above. $R^{12}$ is independently -halo, —$NO_2$, —CN, —($C_1$–$C_{30}$)hydrocarbyl, —O($C_1$–$C_{30}$)hydrocarbyl, —N(($C_1$–$C_{30}$)hydrocarbyl)$_2$, —Si(($C_1$–$C_{30}$)hydrocarbyl)$_3$, —($C_1$–$C_{30}$)heterohydrocarbyl, -aryl, or -heteroaryl. E, M, m, X, Y, and n in formulae I and II are defined herein.

27 Claims, 7 Drawing Sheets

POLYOLEFIN CATALYST COMPONENT USING NON-COVALENT INTERACTIONS

This application claims the benefit of U.S. Provisional Application No. 60/404,452, filed Aug. 19, 2002, the entire disclosure being incorporated herein by reference.

FIELD OF THE INVENTION

This invention relates to a non-metallocene catalyst system comprising a metal complex and a suitable activator, which is highly active in the olefin polymerization process.

BACKGROUND OF THE INVENTION

Polyolefins have been made chiefly using conventional Ziegler catalyst systems, but in recent years, the replacement of Ziegler catalysts by metallocene-based systems has begun. Metallocene catalysts, which are transition metal compounds bearing one or more cyclopentadienyl ("Cp") ring ligand(s), are typically used with aluminoxanes as activators to give very high activities. In many cases, the transition metal is titanium or zirconium. Metallocene polyolefin catalysts provide solutions to many of the problems encountered for Ziegler catalysts (such as low activity, staining and instability from residual catalysts, broad molecular distribution, and ineffective co-monomer incorporation) and are well known in the art.

The commercialization of metallocene catalysts for olefin polymerization has resulted in great interest in the design of non-metallocene homogeneous catalysts. A new generation of catalysts may display improved activity and offer a superior route to known polyolefins and may also lead to processes and products that are outside the capability of metallocene catalysts. In addition, substituted analogues of non-cyclopentadienyl ligands and compounds may be easier to synthesize and hence non-metallocene catalysts may be more cost-effective.

Non-metallocene polyolefin catalysts with at least one phenolate group are well known in the art (see U.S. Pat. No. 4,452,914 to Coleman, III, et al. and U.S. Pat. No. 5,079,205 to Canich). U.S. Pat. No. 5,840,646 to Katayama et al. and EP 0 606 125 B1 assigned to Shell International Research disclose bidentate bis(phenolate) titanium and zirconium catalysts for olefin polymerization.

Multidentate anionic oxygen- and nitrogen-based groups have attracted attention as ligands for non-metallocene polyolefin catalysts. In terms of bidentate ligands, pyridinoxy and quinolinoxy ligands have been reported (see, e.g., U.S. Pat. No. 5,637,660 to Nagy et al.; U.S. Pat. No. 5,852,146 to Reichle et al.; U.S. Pat. No. 6,020,493 to Liu; Bei et al., Organometallics 17:3282 (1997); and Tsukahara et al., Organometallics 16:3303 (1997).)

Tetradentate anionic ligands containing amine-bis(phenolate) groups (phenolate being an aromatic hydroxyl group) have recently been applied in polyolefin catalysts by Kol, Goldschmidt and coworkers (see U.S. Pat. No. 6,333,423 to Kol et al.; Tshuva et al., Chem. Commun. 379 (2000) and Chem. Commun. 2120 (2001)). Shao et al., Organometallics 19:509 (2000) describe zirconium complexes of tridentate chelating amine-bis(alkoxide) (alkoxide being an aliphatic hydroxyl group) ligands as polyolefin catalysts, but the observed activity is very low. Bouwkamp et al., Organometallics 17:3645 (1998) described zirconium complexes with symmetric tridentate amine-bis(σ-aryl) dianionic ligands as polyolefin catalysts, but the observed activities are only moderate.

Hence there is a need in the art for new olefin polymerization catalysts, particularly catalysts containing multidentate ligands of the pyridine-phenolate type. There is also a need in the art for the discovery and optimization of non-metallocene polyolefin catalysts containing unsymmetric or chiral ligands, because this may result in the stereoselective polymerization of 1-olefins (alpha-olefins) and lead to polyolefins with distinctive morphology and properties.

Metallocene catalysts, especially those that are chiral and/or of low symmetry, are used to produce stereoregular polyolefins (see, e.g., G. W. Coates, Chem. Rev. 100:1223 (2000), and references cited therein). These catalysts depend on simple steric effects to control stereoselectivity.

Use of weak non-covalent attractive interactions to achieve stereoselectivity has not been established in the art. Use of weak non-covalent attractive interactions to stabilize reactive intermediates in olefin polymerization has not been established in the art.

SUMMARY OF THE INVENTION

This invention relates to a polyolefin catalyst system, which comprises a cyclometallated catalyst containing a Group 3 to 10 metal atom or lanthanide metal and a suitable activator.

This invention also relates to cyclometallated catalysts of formula I shown below:

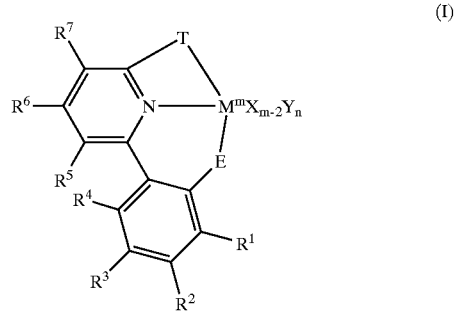

wherein:
R$^1$–R$^7$ are each independently —H, -halo, —NO$_2$, —CN, —(C$_1$–C$_{30}$)hydrocarbyl, —O(C$_1$–C$_{30}$)hydrocarbyl, —N((C$_1$–C$_{30}$)hydrocarbyl)$_2$, —Si((C$_1$–C$_{30}$)hydrocarbyl)$_3$, —(C$_1$–C$_{30}$)heterohydrocarbyl, -aryl, or -heteroaryl, each of which may be unsubstituted or substituted with one or more —R$^8$ groups; or two R$^1$–R$^7$ may be joined to form cyclic group;

R$^8$ is -halo, —(C$_1$–C$_{30}$)hydrocarbyl, —O(C$_1$–C$_{30}$)hydrocarbyl, —NO$_2$, —CN, —Si((C$_1$–C$_{30}$)hydrocarbyl)$_3$, —N((C$_1$–C$_{30}$)hydrocarbyl)$_2$, —(C$_1$–C$_{30}$)heterohydrocarbyl, -aryl, or -heteroaryl;

T is —CR$^9$R$^{10}$— wherein R$^9$ and R$^{10}$ are defined as for R$^1$ above;

E is a Group 16 element;

M is a metal selected from the group consisting of metallic Group 3 to Group 10 elements and the Lanthanide series elements;

m is the oxidation state of the M;

X is defined as R$^1$ above excluding —H, wherein X is bonded to M;

Y is neutral ligand datively bound to M; and n is an integer ranging from 0 to 5.

This invention further relates to cyclometallated catalysts of formula II shown below:

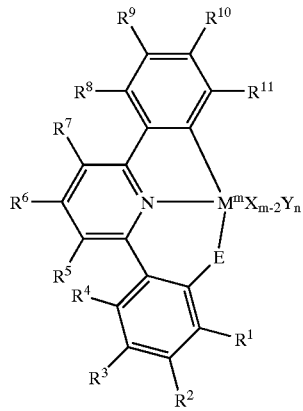

(II)

wherein:

$R^1$–$R^{11}$ each independently —H, -halo, —$NO_2$, —CN, —($C_1$–$C_{30}$)hydrocarbyl, —O($C_1$–$C_{30}$)hydrocarbyl, —N(($C_1$–$C_{30}$)hydrocarbyl)$_2$, —Si(($C_1$–$C_{30}$)hydrocarbyl)$_3$, —($C_1$–$C_{30}$)heterohydrocarbyl, -aryl, -heteroaryl, each of which may be unsubstituted or substituted with one or more —$R^{12}$ groups; or two $R^1$–$R^7$ may be joined to form a cyclic group;

each $R^{12}$ is independently -halo, —$NO_2$, —CN, —($C_1$–$C_{30}$)hydrocarbyl, —O($C_1$–$C_{30}$)hydrocarbyl, —N(($C_1$–$C_{30}$)hydrocarbyl)$_2$, —Si(($C_1$–$C_{30}$)hydrocarbyl)$_3$, —($C_1$–$C_{30}$)heterohydrocarbyl, -aryl, or -heteroaryl;

E is a Group 16 element;

M is a metal selected from the group consisting of metallic Group 3 to Group 10 elements and the Lanthanide series elements;

m is the oxidation state of the M;

X is $R^1$ excluding —H, wherein X is bonded to M;

Y is neutral ligand datively bound to M; and n is an integer ranging from 0 to 5.

In one embodiment, the cyclometallated catalysts of formula (I) and/or formula (II) are combined with a suitable activator to form an olefin polymerization catalyst.

In one embodiment, the cyclometallated catalysts of formula (I) and/or formula (II) are combined with a suitable activator to form a catalyst useful for the stereoselective polymerization of 1-olefins.

In one embodiment, the $R^1$–$R^7$ and T groups in formula I, and the $R^1$–$R^{11}$ groups in formula II exhibit weak attractive non-covalent interactions with the polymer chain.

The invention further relates to methods of olefin polymerization comprising cyclometallated catalysts of formula I and/or II. Such polymerization processes include but are not limited to gas, high-pressure liquid, slurry, bulk, solution, or suspension-phase techniques, and combinations thereof.

BRIEF DESCRIPTION OF THE DRAWINGS

FIG. 1 also shows the $^1$NMR spectra for the diastereotopic methylene hydrogens of the benzyl group of Catalyst 3 in $C_6D_6$, $CD_2Cl_2$ and $d_8$-THF, demonstrating the effect of solvent polarity on the chemical shift and splitting pattern, where the designation "{$^{19}$F}" means the NMR spectrum was run in $^{19}$F decoupled mode.

DETAILED DESCRIPTION OF THE INVENTION

Figure 1:
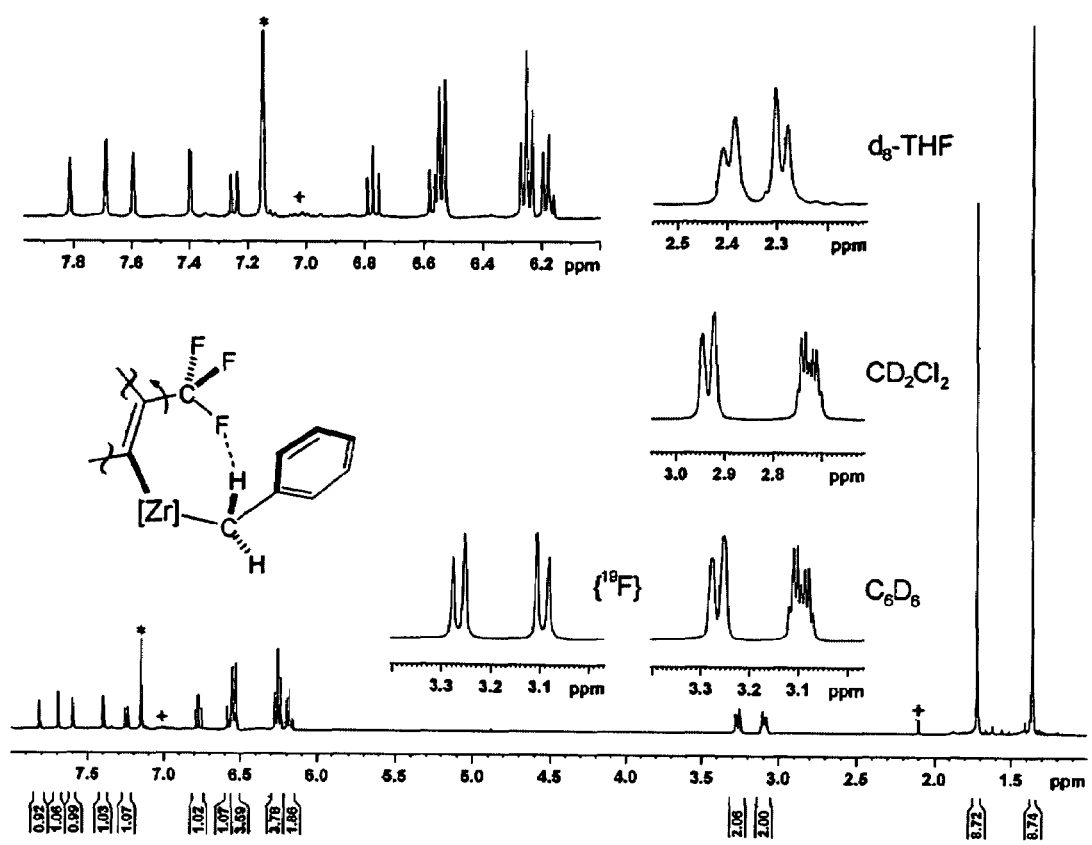
FIG. 1 shows the $^1$H NMR spectrum of Catalyst 3 in $C_6D_6$, (400 MHz, 300 K) (*=$C_6D_6$, +=residual toluene).

As used herein, the term "—($C_1$–$C_{30}$)hydrocarbyl" refers to a hydrocarbon group containing from 1–30 carbon atoms. Non-limiting examples of —($C_1$–$C_{30}$)hydrocarbyl groups include —($C_1$–$C_{30}$)alkanes; —($C_1$–$C_{30}$)alkenes; —($C_1$–$C_{30}$)alkynes.

As used herein, the term "—($C_1$–$C_{30}$)heterohydrocarbyl" refers to a —($C_1$–$C_{30}$)hydrocarbyl in which one or more of the carbon atoms have been replaced with an atom other than carbon or hydrogen, i.e., a heteroatom, e.g., N, P, Si, Ge, O and S.

As used herein the term "heteroaryl" refers to an aryl group containing an atom other than carbon in the aryl ring. Non-limiting examples of heteroaryls include pyrrole, pyridine, and the like.

As used herein, the phrase "alkylaluminum compound" refers to a compound containing a bond between an organic radical and an aluminum metal.

As used herein, the phrase "homopolymerization process" means a process for forming a polyolefin using only one type of monomer. The resultant polymer is referred to as a "homopolymer."

As used herein, the phrase "copolymerization process" means a polymerization process in which two or more different olefin monomers are incorporated into the same polymer to form a "copolymer."

As used herein, the phrase "cyclometallated catalyst" means a compound in which the metallic Group 3 to Group 10 or Lanthanide elements is part of a ligand-metal ring system containing from 4 to 8 atoms, wherein the ligand-metal ring system contains a metal-carbon [M—C] bond. The ring system is stabilized due to the chelate effect, i.e., the ligand is coordinated to the metal by at least two bonds.

As used herein, the phrase "neutral ligand" refers to an uncharged molecule, which may be either a mono- or bidentate molecule, that forms a dative bond between a ligand atom and the metal atom. Non-limiting examples of neutral ligands include N-donor ligands, e.g., amines, tetrahydropyrrole, pyrrole, piperazine and pyridine; P-donor groups, e.g., phosphine, tetrahydrophosphole, and phosphole; O-donor groups include, e.g., ethers including dimethyl ether, diethyl ether, di-propyl ether, di-butyl ether, di-pentyl ether, tetrahydrofuran and dioxane; and glymes, e.g., dimethoxyethane.

As used herein, the phrase "non-nucleophilic anions" refers to the anion portion of an activator salt, which is a weak or poor Lewis base.

As used herein, the term "olefin" refers to a hydrocarbon molecule containing at least one carbon—carbon double bond such as, e.g., ethylene. The olefin may be unsubstituted or substituted, provided the substituents do not prevent the polymerization of the olefin.

As used herein, the phrase "Group 16 element" refers to oxygen, sulfur, selenium and tellurium.

As used herein, the term "halide" refers to fluoride, chloride, bromide and iodide.

This invention relates to a polyolefin catalyst system comprising a cyclometallated catalyst and a suitable activator, wherein the metal is a Group 3 to 10 transition metal or lanthanide metal. [A cyclometallated catalyst contains a metal-carbon [M-C] bond as part of a [X-M-C] ring system which is stabilized due to the chelate effect, where X can be any element or group that is capable of bonding to the metal.] Preferably the metal is Ti, Zr or Hf.

This invention also relates to cyclometallated catalysts of formula I:

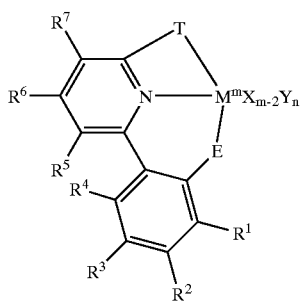

(I)

wherein:
$R^1$–$R^7$ are each independently —H, -halo, —$NO_2$, —CN, —($C_1$-$C_{30}$)hydrocarbyl, —O($C_1$-$C_{30}$)hydrocarbyl, —N(($C_1$-$C_{30}$)hydrocarbyl)$_2$, —Si(($C_1$-$C_{30}$)hydrocarbyl)$_3$, —($C_1$-$C_{30}$)heterohydrocarbyl, -aryl, or -heteroaryl, each of which may be unsubstituted or substituted with one or more —$R^8$ groups; or two $R^1$–$R^7$ may be joined to form a cyclic group;

$R^8$ is -halo, —($C_1$-$C_{30}$)hydrocarbyl, —O($C_1$-$C_{30}$)hydrocarbyl, —$NO_2$, —CN, —Si(($C_1$-$C_{30}$)hydrocarbyl)$_3$, —N(($C_1$-$C_{30}$)hydrocarbyl)$_2$, —($C_1$-$C_{30}$)heterohydrocarbyl, -aryl, or -heteroaryl;

T is —$CR^9R^{10}$— wherein $R^9$ and $R^{10}$ are defined as for $R^1$ above;

E is a Group 16 element;

M is a metal selected from the group consisting of metallic Group 3 to Group 10 elements and the Lanthanide series elements;

m is the oxidation state of the M;

X is $R^1$ excluding —H, wherein X is bonded to M;

Y is neutral ligand datively bound to M; and n is an integer ranging from 0 to 5.

In one embodiment, the invention relates to catalysts of formula I wherein M is titanium, zirconium or hafnium.

In one embodiment, the invention relates to catalysts of formula I wherein E is —O— such that a tridentate phenolate-pyridine-carbanion ligand is coordinated to M.

In one embodiment, the invention relates to catalysts of formula I wherein X is —$CH_3$, —$CH_2CH_3$, -benzyl, -halo. Preferably, X is -benzyl, or -chloride.

In one embodiment, the invention relates to catalysts of formula I wherein Y is absent.

In one embodiment, the invention relates to catalysts of formula I wherein Y is an N-donor ligand, P-donor ligand, As-donor ligand, O-donor ligand or S-donor ligand. Non-limiting examples of neutral ligands include N-donor ligands, e.g., amines, tetrahydropyrrole, pyrrole, piperazine and pyridine; P-donor groups, e.g., trialkylphosphine, dialkylarylphosphine, alkyldiarylphosphine and triarylphosphine, in which one or more of the alkyl or aryl groups may be replaced by an alkoxy or aryloxy group to form a phosphite; As-donor group include, e.g., trialkylarsine, dialkylarylarsine, alkyldiarylarsine, and triarylarsine, in which one or more of the alkyl or aryl groups may be replaced by an alkoxy or aryloxy group to form an arsite; O-donor groups, e.g., ethers including dimethyl ether, diethyl ether, dipropyl ether, di-butyl ether, di-pentyl ether, tetrahydrofuran, dioxane; and glymes, e.g., dimethoxyethane. In a preferred embodiment, Y is tetrahydrofuran or diethyl ether. More preferably, Y is tetrahydrofuran.

In one embodiment, the invention relates to catalysts of formula I, wherein the $R^1$–$R^7$ and T groups exhibit weak attractive non-covalent interactions with the polymer chain. Without being bound by theory, it is believed that weak non-covalent attractive interactions must avoid interactions that might otherwise disrupt the polymerization process and/or the turnover rate. Evidence for intramolecular weak non-covalent attractive interactions have been obtained for the non-metallocene polyolefin catalysts described herein.

This invention also relates to non-metallocene catalysts of formula (II):

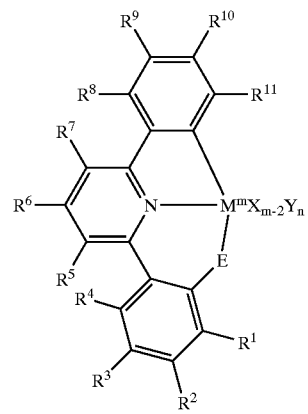

(II)

wherein:
$R^1$–$R^{11}$ each independently —H, -halo, —$NO_2$, —CN, —($C_1$-$C_{30}$)hydrocarbyl, —O($C_1$-$C_{30}$)hydrocarbyl, —N(($C_1$-$C_{30}$)hydrocarbyl)$_2$, —Si(($C_1$-$C_{30}$)hydrocarbyl)$_3$, —($C_1$-$C_{30}$)heterohydrocarbyl, -aryl, -heteroaryl, each of which may be unsubstituted or substituted with one or more —$R^{12}$ groups; or two $R^1$–$R^7$ may be joined to form a cyclic group;

each $R^{12}$ is independently -halo, —$NO_2$, —CN, —($C_1$-$C_{30}$)hydrocarbyl, —O($C_1$-$C_{30}$)hydrocarbyl, —N(($C_1$–$C_{30}$)hydrocarbyl)$_2$, —Si(($C_1$–$C_{30}$)hydrocarbyl)$_3$, —($C_1$–$C_{30}$)heterohydrocarbyl, -aryl, or -heteroaryl;

E is a Group 16 element;

M is a metal selected from the group consisting of metallic Group 3 to Group 10 elements and the Lanthanide series elements;

m is the oxidation state of the M;

X is $R^1$ excluding —H, wherein X is bonded to M;

Y is neutral ligand datively bound to M; and n is an integer ranging from 0 to 5.

In one embodiment, the invention relates to catalysts of formula II wherein M is titanium, zirconium or hafnium.

In one embodiment, the invention relates to catalysts of formula II wherein E is —O— such that a tridentate phenolate-pyridine-carbanion ligand is coordinated to M.

In one embodiment, the invention relates to catalysts of formula II wherein X is —$CH_3$, —$CH_2CH_3$, -benzyl or -halo. Preferably, X is -benzyl or -chloride.

In one embodiment, the invention relates to catalysts of formula II wherein Y is absent.

In one embodiment, the invention relates to catalysts of formula II wherein Y is as defined above for the catalysts of formula I. In a preferred embodiment, Y is tetrahydrofuran.

In one embodiment, the invention relates to catalysts of formula II wherein M is Zr; $R^1$ and $R^3$ are —C($CH_3$)$_3$; $R^2$ and $R^4$–$R^{11}$ are —H; E is —O—; m is 4; X is —$CH_2(C_6H_5)$; and n is 0.

In one embodiment, the invention relates to catalysts of formula II wherein M is Zr; $R^1$ and $R^3$ are —C($CH_3$)$_3$; $R^2$ and $R^4$–$R^{11}$ are —H; E is —O—; m is 4; X is —Cl; n is 1; and Y is -tetrahydrofuran.

In one embodiment, the invention relates to catalysts of formula II wherein M is Zr; $R^1$ and $R^3$ are —C($CH_3$)$_3$; $R^9$ and $R^{11}$ are —$CF_3$; $R^2$, $R^4$–$R^8$ and $R^{10}$ are —H; E is —O—; m is 4; X is —$CH_2(C_6H_5)$; and n is 0.

In one embodiment, the invention relates to catalysts of formula II wherein M is Ti; $R^1$ and $R^3$ are —C($CH_3$)$_3$; $R^9$ and $R^{11}$ are —$CF_3$; $R^2$, $R^4$–$R^8$ and $R^{10}$ are —H; E is —O—; m is 4; X is —$CH_2(C_6H_5)$; and n is 0.

In one embodiment, the invention relates to catalysts of formula II wherein M is Zr; $R^1$ and $R^3$ are —C($CH_3$)$_3$; $R^9$ is —$CF_3$; $R^2$, $R^4$–$R^8$ and $R^{10}$–$R^{11}$ are —H; E is —O—; m is 4; X is —$CH_2(C_6H_5)$; and n is 0.

In one embodiment, the invention relates to catalysts of formula II wherein M is Zr; $R^1$ and $R^3$ are —C($CH_3$)$_3$; $R^9$ is —$CF_3$; $R^{11}$ is —F; $R^2$, $R^4$–$R^8$ and $R^{10}$ are —H; E is —O—; m is 4; X is —Cl; n is 1; and Y is tetrahydrofuran.

In one embodiment, the invention relates to catalysts of formula II wherein the $R^1$–$R^{11}$ groups in formula II exhibit weak attractive non-covalent interactions with the polymer chain. Without being bound by theory, it is believed that weak non-covalent attractive interactions must avoid interactions that might otherwise disrupt the polymerization process and/or the turnover rate. Evidence for intramolecular weak non-covalent attractive interactions have been obtained for the non-metallocene polyolefin catalysts described herein.

Figure 2:
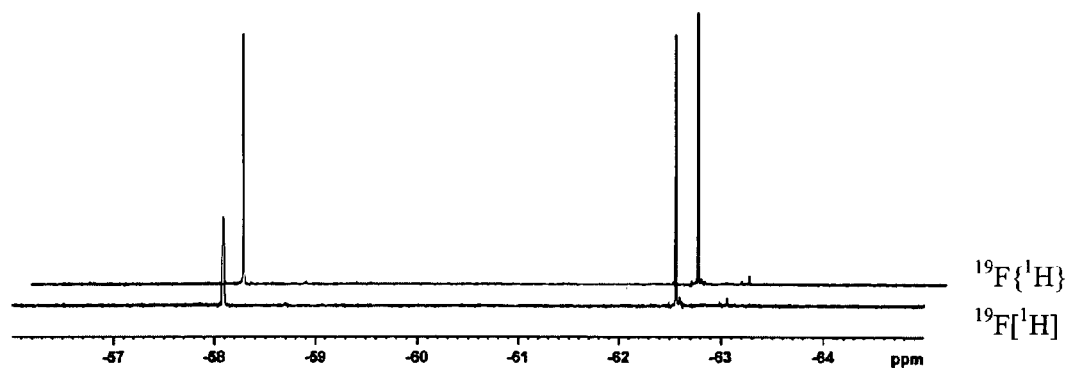
FIG. 2 shows the $^{19}$F[$^1$H] (front) and $^{19}$F{$^1$H} (back; horizontal scale displaced for clarity) NMR spectra (376 MHz, $C_6D_6$, 300 K) of Catalyst 3. The designation "[ ]" means that the NMR spectrum was run in coupled mode (i.e., $^{19}$F and $^1$H coupled NMR).
Figure 3:
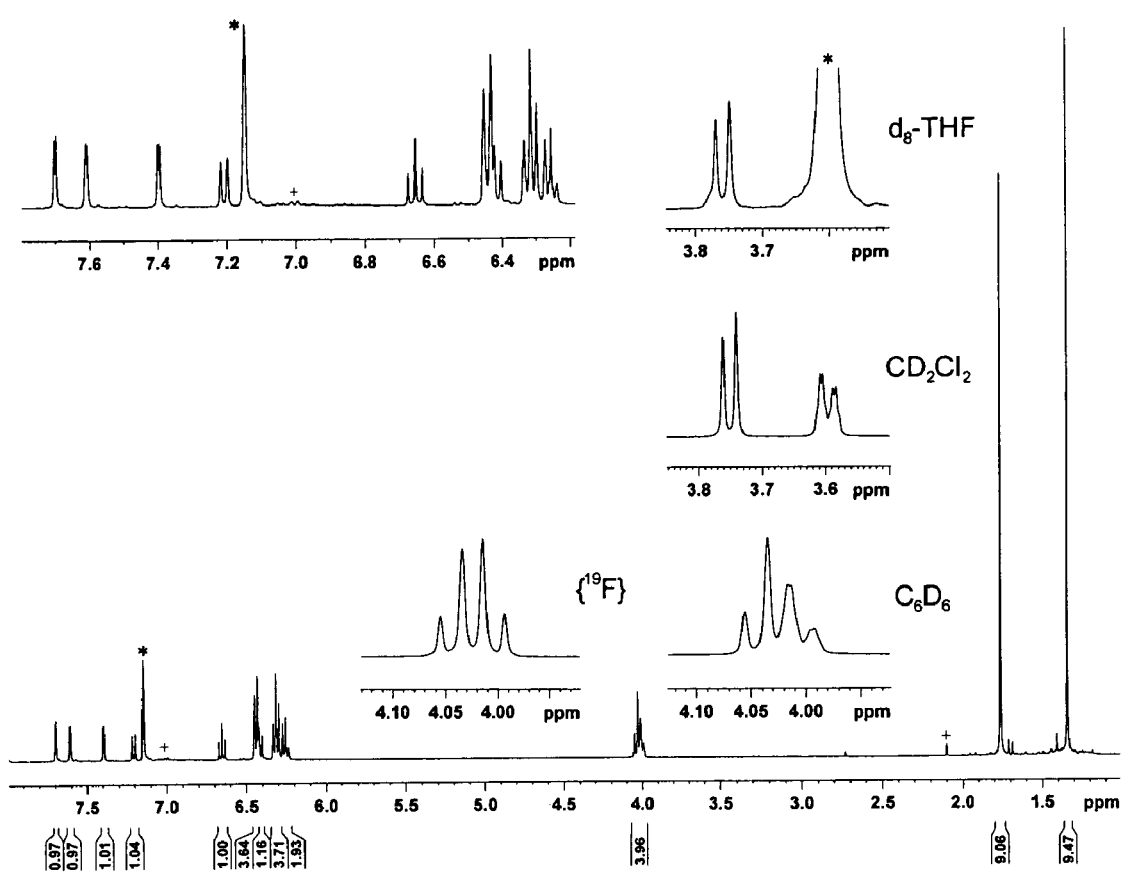
FIG. 3 shows the $^1$H NMR spectra (400 MHz, 300 K) of Catalyst 4, illustrating the effects of $^{19}$F-decoupling and solvent polarity upon the diastereotopic methylene hydrogens (*=deuterated solvent, +=residual toluene) for $C_6D_6$, $CD_2Cl_2$ and $d_8$-THF.

In one embodiment, the invention relates to a catalyst of formula II (one non-limiting example being depicted as Catalyst 3 in Example 6) wherein M is Zr; E is —O—; X is -benzyl; $R^9$ and $R^{11}$ are —$CF_3$; $R^1$ and $R^3$ are -tert-butyl; $R^{2,4-8,10}$ are —H; and Y is absent. In this embodiment, $^1$H J(H . . . F) coupling of 3.3 Hz ($^1$H NMR, see FIG. 1) and $^2$H J(C . . . F) coupling of 5.9 Hz ($^{13}$C NMR) are observed between one of the benzyl —$CH_2$— protons and the —$CF_3$ group at $R^{11}$. Subsequent $^{19}$F-decoupling of the $^1$H NMR spectrum confirms this coupling. Similarly, while the coupling in the $^{19}$F[1H] NMR spectrum is not clearly resolved, the $^{19}$F{1H} spectrum undergoes significant narrowing for the downfield resonance at –58.09 ppm for the —$CF_3$ group at $R^{11}$ only (FIG. 2). These observations thus demonstrate the existence of intramolecular 'through-space' coupling via weak non-covalent attractive [C—H . . . F—C] hydrogen bonding interactions. The effects of solvent polarity upon this coupling have been probed, and $^1$H J(H . . . F) values of 3.3 and 3.1 Hz in $C_6D_6$ and $CD_2Cl_2$ respectively have been obtained, whereas in d8-THF the said coupling is unresolved yet still apparent (FIG. 1). A virtually identical intramolecular [CH . . . FC] interaction is obtained when a catalyst of formula II is used in which the Zr of Catalyst 3 is replaced by Ti (one non-limiting example being depicted as Catalyst 4 in Example 7), as indicated by analogous NMR experiments (FIG. 3), although the through-space coupling is slightly weaker (in $C_6D_6$: $^{1h}J_{HF}$ ca. 2 Hz, $^{2h}J_{CF}$=5.3 Hz).

This model can be applied to an active intermediate during olefin polymerization, where intramolecular attractive weak interactions (e.g. C—H . . . F—C) can be envisaged between the functionalized ligand and polymer chain. Use of said weak non-covalent interactions to modify or manipulate catalytic reactivity and polymer properties has not been established in the art. Use of said weak non-covalent interactions to stabilize reactive intermediates or to achieve stereoselectivity in olefin polymerization has not been established in the art. For example, these types of intramolecular weak non-covalent attractive interactions can suppress H-transfer and chain termination processes during polymerization and may also afford highly stereoselective polymers.

The preparation of the desired ligands is versatile and can be achieved by modification of procedures described in the literature (see, e.g., Silva et al., *Tetrahedron* 53:11645 (1997); and Dietrich-Buchecker et al., *Tetrahedron* 46: 503 (1990)).

Metallation of the substituted 2-(phenol)-6-arylpyridine substrates containing acidic protons can be accomplished by reaction with basic metal reagents such as tetrabenzyltitanium(IV), Ti(CH$_2$Ph)$_4$, tetrabenzylzirconium(IV), Zr(CH$_2$Ph)$_4$, bisbenzylzirconium(IV) dichloride, Zr(CH$_2$Ph)$_2$Cl$_2$, and tetrabenzylhafnium(IV), Hf(CH$_2$Ph)$_4$, which is accompanied by elimination of toluene and cyclometallation, i.e., metal-carbon bond formation between metal and aryl group) readily occurs at room temperature. The resultant metal complex contains a phenolate-pyridine-carbanion ligand which is chelated in a tridentate meridional fashion. A neutral O-donor solvent, for example tetrahydrofuran or diethyl ether, is added to the reaction mixture to facilitate the isolation of the complex, in some instances in its solvated form. As determined by $^1$H NMR spectroscopy and in some case by X-ray crystallography, the two remaining halide or alkyl ligands are in a cis conformation, and this is important for the employment of these complexes as polyolefin catalysts.

The present invention relates to a catalyst system comprising the cyclometallated catalysts of the invention and an activator. Generally, the activator converts the cyclometallated catalyst to a cationic active species. Suitable activators are well known in the art and include, but are not limited to, trimethylaluminum (TMA), triethylaluminum (TEA), tri-isobutylaluminum (TIBA), tri-n-octylaluminum, methylaluminum dichloride, ethylaluminum dichloride, dimethylaluminum chloride, diethylaluminum chloride, aluminoxanes, and the like. Aluminoxanes are known in the art as typically the oligomeric compounds that can be prepared by the controlled addition of water to an alkylaluminum compound, for example trimethylaluminum. Examples of aluminoxanes compounds include methylaluminoxane (MAO), modified methylaluminoxane (MMAO), ethylaluminoxane, and diisobutylaluminoxane. In this invention, alkylaluminoxanes such as methylaluminoxane (MAO) are preferred. In this context it should be noted that the term "alkylaluminoxane" as used in this specification includes alkylaluminoxanes available commercially which may contain a proportion, typically about 10 wt %, but optionally up to 50 wt %, of the corresponding trialkylaluminum; for instance, commercial MAO usually contains approximately 10 wt % trimethylaluminum (TMA), whilst commercial MMAO contains both TMA and TIBA. Quantities of alkylaluminoxane quoted herein include such trialkylaluminum impurities, and accordingly quantities of trialkylaluminum compounds quoted herein are considered to comprise compounds of the formula $AlR_3$ additional to any $AlR_3$ compound incorporated within the alkylaluminoxane when present.

Suitable activators also include acid salts that contain non-nucleophilic anions. These compounds generally consist of bulky ligands attached to boron or aluminum. Non-limiting examples of suitable activators include tetrakis(pentafluorophenyl)borate, dimethylphenylammonium tetra(pentafluorophenyl)borate, trityl tetra(pentafluorophenyl) borate, and the like. Suitable activators also include trialkyl or triarylboron compounds such as tris(pentafluorophenyl)boron, tris(pentabromophenyl)boron, and the like. Other suitable activators are described, for example, in U.S. Pat. Nos. 5,064,802 and 5,599,761 to Turner.

In one embodiment, the activator is selected from the group consisting of trimethylaluminum, triethylaluminum, tri-isobutylaluminum, tri-n-octylaluminum, methylaluminum dichloride, ethylaluminum dichloride, dimethylaluminum chloride, diethylaluminum chloride, aluminoxanes, tetrakis(pentafluorophenyl)borate, dimethylphenylammonium tetra(pentafluorophenyl)borate, trityl tetra(pentafluorophenyl)borate, tris(pentafluorophenyl)boron, tris(pentabromophenyl)boron, and mixtures thereof.

In the preparation of the catalysts of the present invention, the quantity of the activator to be employed is determined by routine experimentation. It is found that the quantity employed is 0.1 to 20,000, preferably 1 to 2000 of mole aluminum (or boron) per mole cyclometallated compound.

In a preferred embodiment, the polyolefin catalyst of formula I and/or formula II is combined with one of more of the above-named activators, or a mixture thereof, to form a cyclometallated catalyst system that is active for olefin polymerization process.

The present invention further relates to methods for polymerizing an olefin using a cyclometallated catalyst system. Such polymerization processes include, but are not limited to, gas-phase, high-pressure liquid, slurry, bulk, solution, or suspension-phase techniques, and combinations thereof. Such processes can be used to perform homopolymerization and/or copolymerization of olefins.

Suitable olefins include one or more of ethylene, propylene, butenes, pentenes, hexenes, octenes, styrenes, 1,3-butadiene, norbornene and the like, either substituted or unsubstituted, or combinations thereof. Suitable substituents are those that will not prevent polymerization of the olefin. Non-limiting examples of suitable olefin substituents include -alkyl, -aryl and —Si(alkyl)$_3$.

In one embodiment, the olefin is selected from the group consisting of ethylene, propylene, 1-butene, 2-pentene, 1-hexene, 1-octene, styrene, 1,3-butadiene, norbornene, and mixtures thereof.

In one embodiment, an olefin selected from the group consisting of ethylene, propylene, or a mixture thereof is copolymerized with an olefin selected from the group consisting of 1-butene, 1-hexene, and 1-octene.

Preferably, the olefin is ethylene or 1-hexene.

In one embodiment, a homopolymer of ethylene is produced.

In another embodiment, a homopolymer of 1-hexene is produced.

The cyclometallated catalyst system of the present invention can also include one of more other transition metal compounds, such as conventional Ziegler catalysts, metallocene catalysts, constrained geometry catalysts, or heat-activated supported chromium oxide (e.g., Phillips-type) catalysts.

The cyclometallated catalysts of formula (I) and formula (II) and/or cyclometallated catalyst systems are optionally used with an inorganic solid or organic polymer support. Suitable supports include silica, alumina, magnesia, titania, clays, zeolites, polymeric supports such as polyethylene, polypropylene, polystyrene, functionalized polystyrene and the like. The supports can be pretreated thermally or chemically to improve catalyst productivity or product properties. The cyclometallated catalysts, activators or cyclometallated catalysts can be deposited on the support in any desired manner. For example, the catalyst can be dissolved in a solvent, combined with a suitable support and, optionally, dried. Alternatively, an incipient-wetness technique can be used. Moreover, the support can simply be introduced into the reactor separately from the catalyst.

As noted above, the cylometallated catalyst can be used in a variety of well-known olefin polymerization processes, including gas, high-pressure liquid, slurry, bulk, solution, or suspension-phase techniques, and combinations of these. The liquid phase process comprises the steps of contacting an olefin monomer with the cyclometallated catalyst system in a suitable polymerization solvent and reacting said monomer in the presence of said cyclometallated catalyst system for a time and at a temperature and pressure sufficient to produce a polyolefin. The pressures used typically range from about 10 psi to about 15,000 psi. Polymerization temperatures range from about $-100°$ C. to about $300°$ C. More preferably, the polymerization temperature ranges from about $-80°$ C. to about $200°$ C. Most preferably, the polymerization temperature ranges from about from about $-60°$ C. to about $100°$ C.

The polymerization process of the present invention is highly productive, i.e., very small quantities of the catalysts are consumed in the polymerization process. Such highly productive processes are desirable, because the amount of catalysts or residues in the final polymer will be very small, thereby eliminating the need to separate or remove residual catalyst from the polymer product.

In one embodiment, the activity of the ethylene polymerization process of this invention can be greater than 1700 g of polymer per mmol of catalyst per hour per atmosphere of ethylene, which corresponds to a catalyst turnover frequency (TOF) of greater than $6.1 \times 10^4$ per hour per atmosphere of ethylene.

Preferably, the cyclometallated catalysts, activators and cyclometallated catalyst systems are prepared and stored under oxygen- and moisture-free conditions. For example, the preparative reactions are performed with anhydrous solvent and under inert atmosphere, e.g., under helium or nitrogen.

The following examples are set forth to illustrate the present invention, and are not meant to limit the scope of the invention. Those skilled in the art will recognize many variations that are within the spirit of the invention and scope of the claims.

EXAMPLES

All experiments were performed under a nitrogen atmosphere using standard Schlenk techniques and/or in a dry box available from M. Braun (Garching, Germany). $^1$H and $^{13}$C NMR spectra were recorded on a Bruker AVANCE™ 600, 500 DRX, 400 or 300 FT-NMR spectrometer (ppm). $^{19}$F NMR spectra were recorded on the Bruker AVANCE™ 400. Mass spectra (EI and FAB) were obtained on a Finnigan MAT™ 95 mass spectrometer. Polymer melting points were determined using a Perkin Elmer DSC7™. Catalyst activities were measured as grams of polymer per millimole of catalyst per hour per atmosphere. Methylaluminoxane (MAO, 10–15 wt % solution in toluene) was prepared according to U.S. Pat. No. 4,665,208 to Turner.

Example 1

Example 1 describes the synthesis of Intermediate 1:

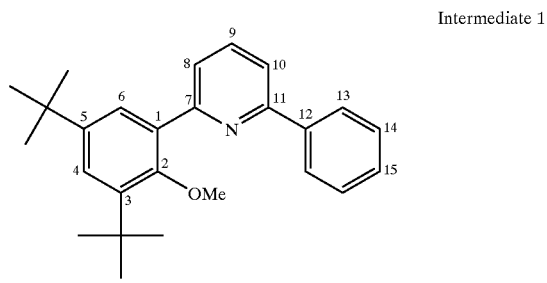

Intermediate 1

Following the procedure described in Silva et al., Tetrahedron 53: 11645 (1997), a mixture of 3,5-di-tert-butyl-2-methoxyacetophenone (2.000 g, 7.62 mmol) and potassium tert-butoxide (1.700 g, 15.24 mmol) in THF (30 ml) was stirred for 2 hr at room temperature under nitrogen atmosphere. To the resultant pale brown suspension was added a solution of 1-N,N-dimethylamino-3-phenyl-3-oxo-1-propene (1.330 g, 7.62 mmol; prepared from acetophenone) in THF, and the resultant mixture was stirred for 12 hr at room temperature to provide a dark red solution. A 2 M solution of ammonium acetate in acetic acid (30 ml) was added to the solution, THF was removed by distillation over 2 hr, and the resultant mixture was added to CH$_2$Cl$_2$ (100 ml). The organic layer was collected, washed with water to remove excess acetic acid, neutralized with saturated sodium bicarbonate solution, and washed with brine. The organic layer was dried over anhydrous magnesium sulphate, and volatiles removed in vacuo. Flash chromatography of the resultant red oil (silica gel; n-hexane:ethyl acetate (20:1) eluent) followed by solvent evaporation in vacuo afforded Intermediate 1 as a yellow powder. Yield: 1.96 g, 69%.

Intermediate 1: 1H (500 MHz, CDCl3): δ 1.37 (s, 9H, 5-tBu), 1.45 (s, 9H, 3-$^t$Bu), 3.38 (s, 3H, OMe), 7.40–7.44 (m, 2H, H$^6$ and H$^{15}$), 7.49 (t, J=7.8 Hz, 2H, H$^{14}$), 7.64 (d, J=2.6 Hz, 1H, H$^4$), 7.69 and 7.74 (two dd, J=1.2 Hz, J=6.5 Hz, 2H, H$^8$ and H$^{10}$), 7.78 (t, J=7.7 Hz, 1H, H$^9$), 8.13 (d, J=8.0 Hz, 2H, H$^{13}$).

Example 2

Example 2 describes the synthesis of Intermediate 2:

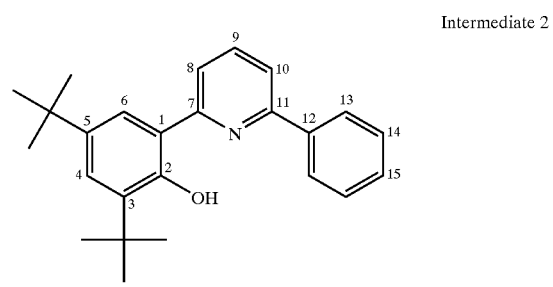

Intermediate 2

Using the procedure described by Dietrich-Buchecker et al., Tetrahedron 46:503 (1990), a mixture of Intermediate 1 (1.670 g, 4.48 mmol) and molten pyridinium chloride (10.347 g, 89.54 mmol) was stirred under N$_2$ atmosphere at 230° C. for 12 hr. The resultant crude-yellow solid was washed with cold n-pentane to afford Intermediate 2 as a yellow solid. Yield: 1.08 g, 67%.

Intermediate 2: $^1$H NMR (500 MHz, CDCl$_3$): δ 1.38 (s, 9H, 5-$^t$Bu), 1.52 (s, 9H, 3-$^t$Bu), 7.43 (d, J=2.4 Hz, 1H, H$^6$), 7.48 (t, J=7.3 Hz, 1H, H$^{15}$), 7.55 (t, J=7.5 Hz, 2H, H$^{14}$), 7.62 (dd, J=2.4 Hz, J=3.8 Hz, 1H, H$^9$), 7.71 (d, J=2.4 Hz, 1H, H$^4$), 7.87–7.91 (m, 2H, H$^8$ and H$^{10}$), 7.97 (d, J=8.6 Hz, 2H, H$^{13}$), 14.75 (s, 1H, OH). $^{13}$C NMR (126 MHz, CDCl$_3$): δ 29.62 (3-CMe$_3$), 31.64 (5-CMe$_3$), 34.36 and 35.35 (CMe$_3$), 118.18 (C$^9$), 118.26 and 138.33 (C$^8$ and C$^{10}$), 121.01 (C$^4$), 126.26 (C$^6$), 126.94 (C$^{13}$), 129.09 (C$^{14}$), 129.43 (C$^{15}$); 4° carbons: 118.03, 137.63, 138.27, 139.79, 154.41, 156.85, 159.03.

FAB-MS (+ve, m/z): 359 [M$^+$].

Example 3

Example 3 describes the synthesis of Catalyst 1:

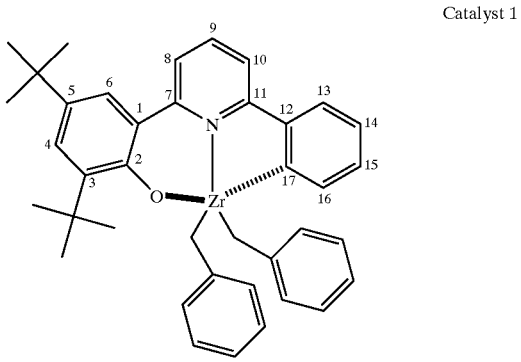

Catalyst 1

A solution of Intermediate 2 (0.400 g, 1.11 mmol) in pentane/diethyl ether (5:1) was slowly added to a stirred solution of Zr(CH$_2$Ph)$_4$ (0.507 g, 1.11 mmol) in pentane/diethyl ether (5:1) at −78° C. The resultant mixture was allowed to warm to room temperature and stirred for 12 hr during which a solution formed. The solution was filtered, concentrated to ca. 10 ml, and stored at −15° C. for 2–3 days to provide orange crystalline solids. Recrystallization from pentane afforded Catalyst 1 as large orange crystals. Yield: 0.53 g, 76%.

Figure 4:
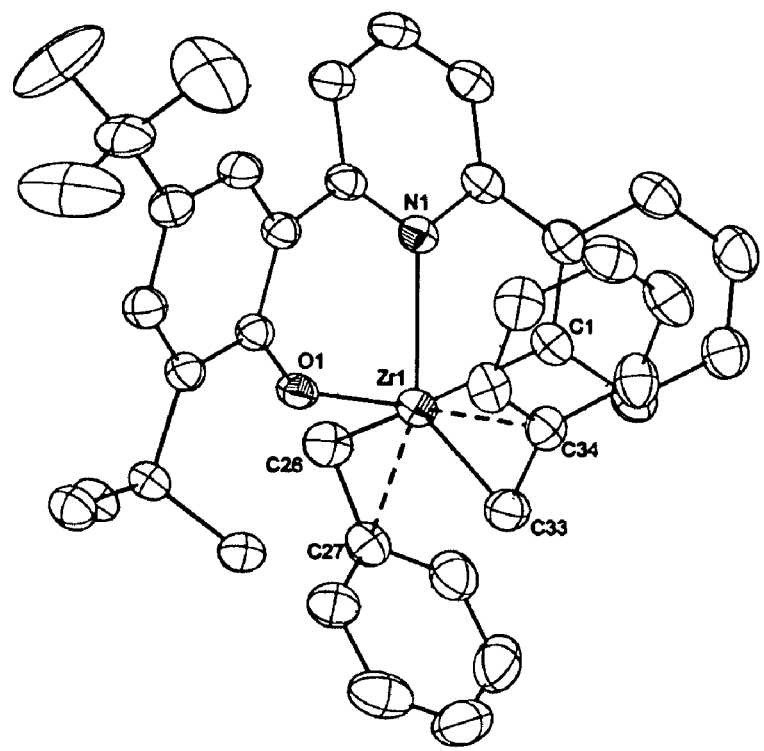
FIG. 4 shows the X-ray crystal structure of Catalyst 1.

Catalyst 1: The X-ray crystal structure for Catalyst 1 (FIG. 4) shows that the benzyl groups are cis to each other. $^1$H NMR (400 MHz, C$_6$D$_6$): δ 1.37 (s, 9H, 5-$^t$Bu), 1.60 (s, 9H, 3-$^t$Bu), 2.40 (d, J=9.3 Hz, 2H, CH$_2$), 2.55 (d, J=9.3 Hz, 2H, CH$_2$), 6.67 (m, 2H, p-Ph), 6.85 (m, 8H, o-Ph and m-Ph), 6.90 (t, J=8.0 Hz, 1H, H$^9$), 7.07 (d, J=8.1 Hz, 1H, H$^{10}$), 7.15 (fused with C$_6$D$_6$, 1H, H$^{14}$), 7.18 (d, J=7.9 Hz, 1H, H$^8$), 7.23 (t, J=7.0 Hz, 1H, H$^{15}$), 7.37 (d, J=7.9 Hz, 1H, H$^{13}$), 7.39 (d, J=2.3 Hz, 1H, H$^6$), 7.63 (d, J=2.3 Hz, 1H, H$^4$), 7.96 (d, J=7.0 Hz, 1H, H$^{16}$). $^{13}$C NMR (126 MHz, C$_6$D$_6$): δ 30.71 (3-CMe$_3$), 32.19 (5-CMe$_3$), 34.90 and 35.89 (CMe$_3$), 66.36 (J$_{CH}$=135.0 Hz, CH$_2$), 116.70 (C$^{10}$), 123.46 (C$^8$), 123.75 (p-Ph), 123.82 (C$^{13}$), 125.67 (C$^6$), 126.85 (C$^4$), 128.90 (C$^{14}$), 129.20 (C$^{15}$), 129.67 and 130.81 (o-Ph and m-Ph), 135.41 (C$^{16}$), 139.27 (i-Ph), 140.10 (C$^9$), 191.65 (C$^{17}$); 40° carbons: 126.89, 136.95, 142.02, 143.99, 156.09, 159.18, 165.07. Anal. Calcd. (%) For C$_{39}$H$_{41}$NOZr (630.98): C, 74.24; H, 6.55; N, 2.22. Found: C, 65.37; H, 6.10; N, 2.47.

Example 4

Example 4 describes the synthesis of Catalyst 2:

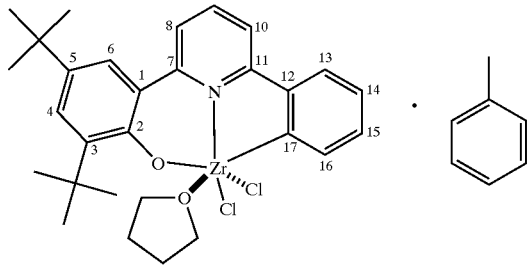

Catalyst 2

A solution of Intermediate 2 (0.270 g, 0.75 mmol) in toluene/THF (5:1). was slowly added to a to a stirred solution of [Zr(CH$_2$Ph)$_2$Cl$_2$(OEt$_2$)(dioxane)$_{0.5}$] (0.350 g, 0.75 mmol) in toluene/THF (5:1) at −78° C. The reaction mixture was allowed to warm up to room temperature and stirred for 12 hr, during which time a yellow solution formed. The solution was filtered, concentrated to ca. 10 ml and stored at −78° C. for 2–3 days. The resultant yellow solid was isolated, recrystallized from toluene, and isolated and dried in vacuo to afford Catalyst 2 with one equivalent of toluene as bright yellow crystals. Yield: 0.36 g, 70%.

Figure 5:
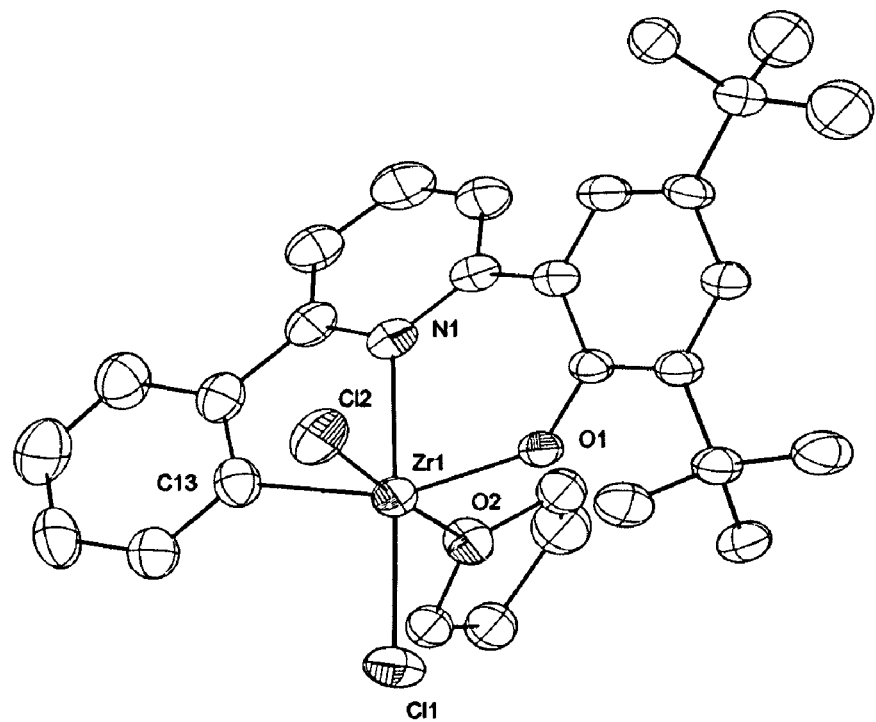
FIG. 5 shows the X-ray crystal structure of Catalyst 2.

Catalyst 2: The X-ray crystal structure for Catalyst 2 (FIG. 5), shows that the chloro groups are cis to each other. $^1$H NMR (500 MHz, CDCl$_3$): δ 1.36 (s, 9H, 5-$^t$Bu), 1.51 (s, 9H, 3-$^t$Bu), 1.66 (br, 4H, thf), 2.35 (s, 3H, PhMe), 3.75 (br, 4H, thf), 7.14–7.24 (m, 5H, PhMe), 7.27–7.32 (m, 2H, H$^{14}$ and H$^{15}$), 7.50 (d, J=2.3 Hz, 1H, H$^6$), 7.54 (d, J=2.3 Hz, 1H, H$^4$), 7.71 (d, J=7.4 Hz, 1H, H$^{16}$), 7.80–7.82 (two d, J=7.8 and 8.2 Hz, 2H, H$^8$ and H$^{10}$), 7.96 (t, J=8.0 Hz, 1H, H$^9$), 8.25 (d, J=6.6 Hz, 1H, H$^{13}$). $^{13}$C NMR (126 MHz, CDCl$_3$): δ 21.48 (PhMe), 25.20 (thf), 30.16 (3-CMe$_3$), 31.62 (5-CMe$_3$), 34.59 and 35.33 (CMe$_3$), 73.76 (thf), 116.80 and 122.98 (C$^8$ and C$^{10}$), 123.06 (C$^{13}$), 124.42 (C$^4$), 125.32, 128.25, 129.06 and 137.92 (PhMe), 127.16 (C$^6$), 128.85 (C$^{14}$), 129.67 (C$^{15}$), 137.04 (C$^{16}$), 140.73 (C$^9$), 187.75 (C$^{17}$); 40° carbons: 124.48, 137.44, 142.69, 142.88, 155.21, 158.01, 164.05. Anal. Calcd. (%) For C$_{36}$H$_{43}$Cl$_2$NO$_2$Zr (683.87): C, 63.23; H, 6.34; N, 2.05. Found: C, 63.31; H, 6.22; N, 2.08.

Example 5

Example 5 describes the synthesis of Intermediate 3:

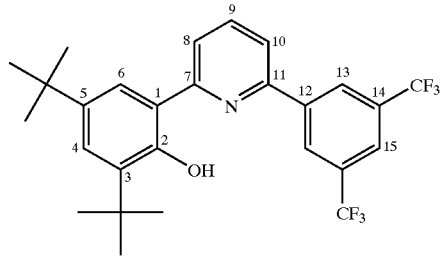

Intermediate 3

Following the procedure described above for preparing Intermediate 1, a mixture of 3,5-di-tert-butyl-2-methoxyacetophenone (1.687 g, 6.43 mmol) and potassium tert-butoxide (1.460 g, 13.00 mmol) in THF (30 ml) was stirred for 2 hr at room temperature under nitrogen atmosphere, and a solution of 1-N,N-dimethylamino-3-(3,5-bis(trifluoromethylphenyl))-3-oxo-1-propene (2.000 g, 6.43 mmol) in THF was added. The resultant mixture was stirred for 12 hr at room temperature during which time a dark red solution formed. A 2M solution of ammonium acetate in acetic acid (30 ml) was added to the solution, THF was removed by distillation over 2 hr, and the resultant mixture was added to CH$_2$Cl$_2$ (100 ml) The organic layer was collected, washed with water to remove excess acetic acid, neutralized with saturated sodium bicarbonate solution, and washed with brine. The organic layer was dried over anhydrous magnesium sulphate, and volatiles removed in vacuo. Reaction of the resultant red oil (1.211 g) with molten pyridinium chloride (4.125 g, 35.70 mmol) under N$_2$ atmosphere at 230° C. for 12 hr as described above in Example 1 yielded a crude yellow solid. The crude solid was then washed with cold n-pentane to afford Intermediate 3 as a yellow solid. Yield: 0.89 g, 70%.

Intermediate 3: $^1$H NMR (500 MHz, CDCl$_3$): δ 1.38 (s, 9H, 5-$^t$Bu), 1.50 (s, 9H, 3-$^t$Bu), 7.46 (d, J=2.4 Hz, 1H, H$^6$), 7.67–7.69 (m, 2H, H$^4$ and H$^9$), 7.95–8.00 (m, 3H, H$^8$, H$^{10}$ and H$^{15}$), 8.39 (s, 2H, H$^{13}$), 13.92 (s, 1H, OH). $^{13}$C NMR (126 MHz, CDCl$_3$): δ 29.58 (3-CMe$_3$), 31.61 (5-CMe$_3$), 31.74 and 34.41 (CMe$_3$), 118.49 (C$^9$), 120.17 and 138.89 (C$^8$ and C$^{10}$), 121.26 (C$^4$), 122.94 (m, C$^{15}$), 126.86 (C$^6$), 127.06 (m, C$^{13}$), 132.58 (q, J$_{CF}$=33.6 Hz, CF$_3$); 40° carbons: 117.93, 137.94, 140.41, 140.52, 151.55, 156.38, 159.88. $^{19}$F NMR (376 MHz, CDCl$_3$): δ −63.39. EI-MS (+ve, m/z): 495 [M$^+$].

Example 6

Example 6 describes the synthesis of Catalyst 3:

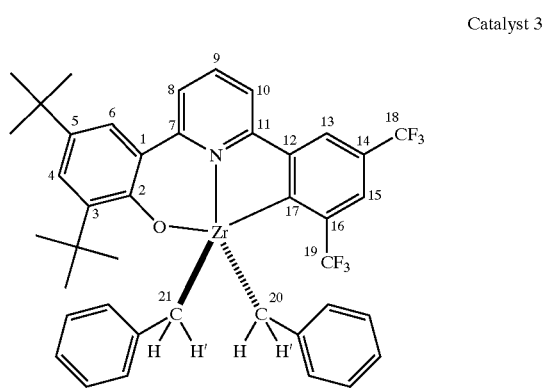

Catalyst 3

A solution of Intermediate 3 (0.200 g, 0.40 mmol) in pentane/diethyl ether (5:1) was slowly added to a stirred solution of $Zr(CH_2Ph)_4$ (0.184 g, 0.40 mmol) in pentane/diethyl ether (5:1) at −78° C. The reaction mixture was allowed to warm up to room temperature and stirred for 12 hr during which time a solution formed. The solution was filtered, concentrated to ca. 10 ml and stored at −15° C. for 2–3 days to provide a red crystalline solid. Recrystallization from pentane afforded Catalyst 3 as large red crystals. Yield: 0.23 g, 75%.

Figure 6:
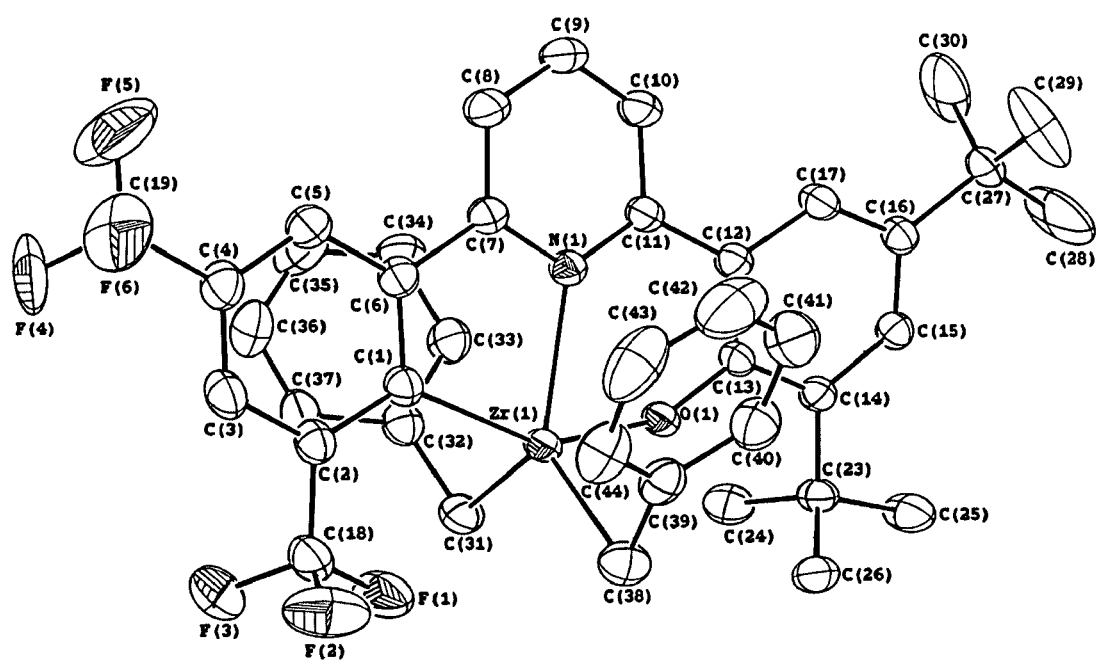
FIG. 6 shows the X-ray crystal structure of Catalyst 3.

Catalyst 3: The X-ray crystal structure for Catalyst 3 (FIG. 6) shows that the benzyl groups are cis to each other. $^1$H NMR (400 MHz, $C_6D_6$): δ 1.36 (s, 9H, 5-$^t$Bu), 1.72 (s, 9H, 3-$^t$Bu), 3.09 (dq, J=9.6 Hz, $^{1h}J_{HF}$=3.3 Hz, 2H, $H^{20'}$ and $H^{21'}$), 3.26 (d, J=9.4 Hz, 2H, $H^{20}$ and $H^{21}$), 6.18 (t, J=7.3 Hz, 2H, p-Ph), 6.25 (t, J=7.7 Hz, 4H, m-Ph), 6.54 (d, J=7.4 Hz, 4H, o-Ph), 6.57 (d, J=7.9 Hz, 1H, $H^{10}$), 6.77 (t, J=8.0 Hz, 1H, $H^9$), 7.25 (d, J=8.0 Hz, 1H, $H^8$), 7.40 (d, J=2.3 Hz, 1H, $H^6$), 7.60 (s, 1H, $H^{13}$), 7.69 (d, J=2.4 Hz, 1H, $H^4$), 7.81 (s, 1H, $H^{15}$). $^{13}$C NMR (126 MHz, $C_6D_6$): δ 31.28 (3-$CMe_3$), 32.12 (5-$CMe_3$), 34.97 and 36.06 ($CMe_3$), 70.50 (q, $^{2h}J_{CF}$=5.9 Hz ($J_{CH}$=133.3 Hz), $C^{20}$ and $C^{21}$), 118.10 ($C^{10}$), 127.64 ($C^4$), 122.08 (br, $C^{15}$), 123.18 (br, $C^{13}$), 123.81 (p-Ph), 124.44 ($C^8$), 125.35 ($C^6$), 129.10 (o-Ph), 129.94 (m-Ph), 130.78 and 138.49 (q, $J_{CF}$=31.1 Hz, $C^{18}$ and $C^{19}$), 136.92 (i-Ph), 139.25 ($C^9$), 189.87 ($C^{17}$); 40° carbons: 126.68, 138.08, 142.78, 145.09, 155.26, 159.33, 161.55. $^{19}$F NMR (376 MHz, $C_6D_6$): δ −58.09 ($F^{19}$), −62.56 ($F^{18}$). EI-MS (+ve, m/z): 765 [M$^+$]. Anal. Calcd. (%) For $C_{41}H_{39}F_6NOZr$ (766.98): C, 64.21; H, 5.13; N, 1.83. Found: C, 63.99; H, 5.57; N, 1.89.]

The NMR data indicate C—F . . . H—C interactions between the —$CF_3$ group ($R^{11}$) and the benzyl groups. The NMR results suggest that intramolecular attractive weak interaction may also occur during polymerization between the —$CF_3$ group and the polymer chain (e.g. C—F . . . H—C). Such weak non-covalent interactions could be advantageously used to affect catalyst reactivity, stabilize reactive intermediates and control polymer properties (e.g., stereoselectivity). For example, these types of intramolecular weak noncovalent attractive interactions can suppress H-transfer and chain termination processes during polymerization and may also afford highly stereoselective polymers.

Example 7

Example 7 describes the synthesis of Catalyst 4:

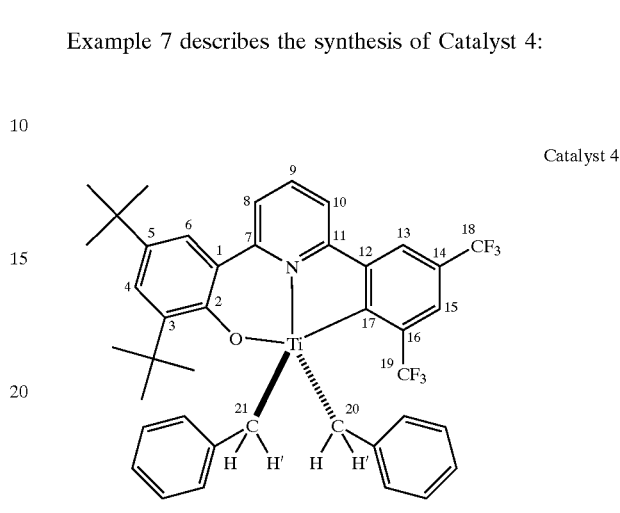

Catalyst 4

A solution of Intermediate 3 (0.214 g, 0.43 mmol) in pentane/diethyl ether (5:1) was slowly added to a stirred solution of $Ti(CH_2Ph)_4$ (0.178 g, 0.43 mmol) in pentane/diethyl ether (5:1) at −78° C. The resultant mixture was allowed to warm to room temperature and stirred for 12 hr during which time a solution formed. The solution was filtered and volatiles removed in vacuo. The resultant crude dark red crystalline solid was recrystallized from pentane to afford Catalyst 4 as dark red crystals. Yield: 0.18 g, 57%.

Catalyst 4: $^1$H NMR (500 MHz, $C_6D_6$): δ 1.34 (s, 9H, 5-$^t$Bu), 1.77 (s, 9H, 3$^t$Bu),), 4.00 (dq, J=8.4 Hz, $^{1h}J_{HF}$=1.2 Hz, 2H, $H^{20'}$ and $H^{21'}$), 4.04 (d, J=8.3 Hz, 2H, $H^{20}$ and $H^{21}$), 6.25 (t, J=7.2 Hz, 2H, p-Ph), 6.32 (t, J=7.1 Hz, 4H, m-Ph), 6.42 (d, J=8.3 Hz, 1H, $H^{10}$), 6.44 (d, J=7.3 Hz, 4H, o-Ph), 6.66 (t, J=8.0 Hz, 1H, $H^9$), 7.21 (d, J=8.0 Hz, 1H, $H^8$), 7.40 (d, J=2.1 Hz, 1H, $H^6$), 7.60 (s, 1H, $H''^3$), 7.70 (d, J=2.3 Hz, 1H, $H^4$), 8.12 (s, 1H, $H^{15}$). $^{13}$C NMR (126 MHz, $C_6D_6$): δ 31.08 (3-$CMe_3$), 31.73 (5-$CMe_3$), 34.70 and 35.71 ($CMe_3$), 96.19 (q, $^{2h}J_{CF}$=5.3 Hz ($J_{CH}$=138.9 Hz), $C^{20}$ and $C^{21}$), 116.58 ($C^{10}$), 122.84 (br, $C^{13}$), 123.19 (br, $C^{15}$), 123.40 ($C^8$), 124.07 (p-Ph), 124.38 ($C^6$), 127.48 ($C^4$), 127.57 (m-Ph), 131.13 and 137.23 (q, $J_{CF}$=32.5 and 30.2 Hz respectively, $C^{18}$ and $C^{19}$), 130.51 (o-Ph), 137.57 (i-Ph), 139.28 ($C^9$), 193.37 ($C^{17}$); 4° carbons: 127.29, 136.99, 143.08, 144.85, Calcd. (%) For $C_{41}H_{39}F_6NOTi$ (723.66): C, 68.05; H, 5.43; N, 1.93. Found: C, 68.08; H, 5.58; N, 2.09.]

The NMR data indicate C—F . . . H—C interactions between the —$CF_3$ group ($R^{11}$) and the benzyl groups. The NMR results suggest that intramolecular attractive weak interaction may also occur during polymerization between the —$CF_3$ group and the polymer chain (e.g. C—F . . . H—C). Such weak non-covalent interactions could be advantageously used to affect catalyst reactivity, stabilize reactive intermediates and control polymer properties (e.g., stereoselectivity). For example, these types of intramolecu

Example 8

Example 8 describes the synthesis of Intermediate 4:

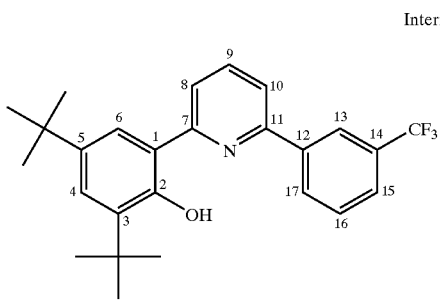

Intermediate 4

Following the procedure described above for preparing Intermediate 1, a mixture of 3,5-di-tert-butyl-2-methoxyacetophenone (2.500 g, 9.53 mmol) and potassium tert-butoxide (2.200 g, 19.06 mmol) in THF (30 ml) was stirred for 2 hr at room temperature under nitrogen atmosphere, and a solution of 1-N,N-dimethylamino-3-(3'-trifluoromethylphenyl)-3-oxo-1-propene (2.315 g, 9.53 mmol) in THF (30 ml) was added. The resultant mixture was stirred for 12 hr during which time a dark red solution formed. A 2M solution of ammonium acetate in acetic acid (30 ml) was added to the solution, THF was removed by distillation over 2 hr, and the resultant mixture was added to $CH_2Cl_2$ (100 ml). The organic layer was collected, washed with water to remove excess acetic acid, neutralized with saturated sodium bicarbonate solution, and washed with brine. The organic layer was dried over anhydrous magnesium sulphate, and volatiles removed in vacuo. The resultant red oil (2.993 g) was then reacted with molten pyridinium chloride (11.760 g, 102 mmol) under $N_2$ atmosphere at 230° C. for 12 hr as described above in Example 1. The resultant crude yellow solid was washed with cold n-pentane to afford Intermediate 4 as a yellow solid. Yield: 2.35 g, 81%.

Intermediate 4: $^1$H NMR (500 MHz, CDCl$_3$): δ 1.38 (s, 9H, 5-$^t$Bu), 1.50 (s, 9H, 3-$^t$Bu), 7.44 (d, J=2.4 Hz, 1H, H$^6$), 7.64 (dd, J=2.5 Hz, J=3.7 Hz, 1H, H$^9$), 7.67–7.69 (m, 2H, H$^4$ and H$^{16}$), 7.73 (d, J=7.8 Hz, 1H, H$^{15}$), 7.91–7.95 (m, 2H, H$^8$ and H$^{10}$), 8.16–8.18 (s and d, 2H, H$^{13}$ and H$^{17}$), 14.36 (s, 1H, OH). $^{13}$C NMR (126 MHz, CDCl$_3$): δ 29.62 (3-CMe$_3$), 31.62 (5-CMe$_3$), 34.39 and 35.37 (CMe$_3$), 118.32 (C$^9$), 119.18 and 138.61 (C$^8$ and C$^{10}$), 121.14 (C$^4$), 123.79 and 126.02 (m, C$^{13}$ and C$^{15}$), 126.55 (C$^6$), 129.76 and 130.33 (C$^{16}$ and C$^{17}$), 131.47 (q, J$_{CF}$=32.3 Hz, CF$_3$); 4° carbons: 117.97, 137.76, 139.15, 140.10, 153.01, 156.63, 159.42. $^{19}$F NMR (376 MHz, CDCl$_3$): δ −63.15. EI-MS (+ve, m/z): 427 [M$^+$].

Example 9

Example 9 describes the synthesis of Catalyst 5:

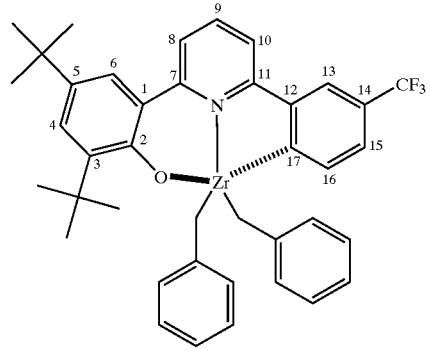

Catalyst 5

A solution of Intermediate 4 (0.251 g, 0.59 mmol) in pentane/diethyl ether (5:1) was slowly added to a stirred solution of Zr(CH$_2$Ph)$_4$ (0.270 g, 0.59 mmol) in pentane/diethyl ether (5:1) at −78° C. The reaction mixture was allowed to warm up to room temperature and stirred for 12 hr during which time a solution formed. The solution was filtered, concentrated to ca. 10 ml and stored at −15° C. for 2–3 days to provide a crude orange-red crystalline solid. Recrystallization from pentane afforded Catalyst 5 as large orange-red crystals. Yield: 0.23 g, 60%.

Figure 7:
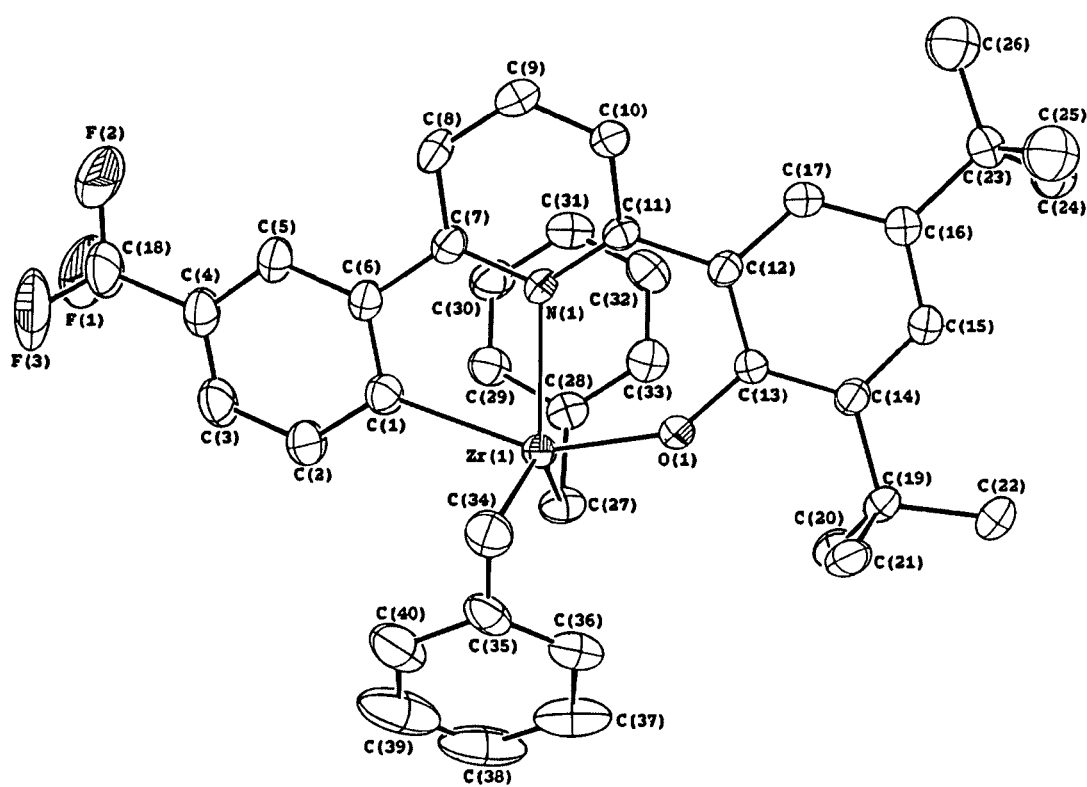
FIG. 7 shows the X-ray crystal structure of Catalyst 5.

Catalyst 5: The X-ray crystal structure for Catalyst 5 (FIG. 7) shows that the benzyl groups are cis to each other. $^1$H NMR (500 MHz, C$_6$D$_6$): δ 1.36 (s, 9H, 5-$^t$Bu), 1.58 (s, 9H, 3-$^t$Bu), 2.27 (d, J=9.3 Hz, 2H, CH$_2$), 2.49 (d, J=9.3 Hz, 2H, CH$_2$), 6.64 (t, J=7.3 Hz, 2H, p-Ph), 6.71 (d, J=7.2, 4H, o-Ph), 6.80 (m, 5H, m-Ph and H$^{10}$), 6.86 (t, J=7.9 Hz, 1H, H$^9$), 7.20 (d, J=7.4 Hz, 1H, H$^8$), 7.39 (d, J=2.3 Hz, 1H, H$^6$), 7.41 (d, J=7.3 Hz, 1H, H$^{15}$), 7.63 (d, J=2.4 Hz, 1H, H$^4$), 7.70 (s, 1H, H$^{13}$), 7.79 (d, J=7.3 Hz, 1H, H$^{16}$). $^{13}$C NMR (126 MHz, C$_6$D$_6$): δ 30.64 (3-CMe$_3$), 32.13 (5-CMe$_3$), 34.93 and 35.85 (CMe$_3$), 66.33 (J$_{CH}$=135.0 Hz, CH$_2$), 117.22 (C$^{10}$), 120.04 (m, C$^{13}$), 124.10 (p-Ph and C$^8$), 124.93 (m, C$^{15}$), 125.71 (C$^6$), 127.12 (C$^4$), 129.55 (o-Ph), 130.04 (q, J$_{CF}$=31.7 Hz, CF$_3$), 131.13 (m-Ph), 136.11 (C$^{16}$), 140.35 (C$^9$), 138.61 (i-Ph), 194.65 (C$^{17}$); 4° carbons: 126.89, 137.01, 142.47, 144.42, 155.75, 159.25, 163.53. $^{19}$F NMR (376 MHz, C$_6$D$_6$): δ −62.27. Anal. Calcd. (%) For C$_{40}$H$_{40}$F$_3$NOZr (698.98): C, 68.73; H, 5.77; N, 2.00. Found: C, 68.21; H, 5.68; N, 2.02.

Example 10

Example 10 describes the synthesis of Intermediate 5:

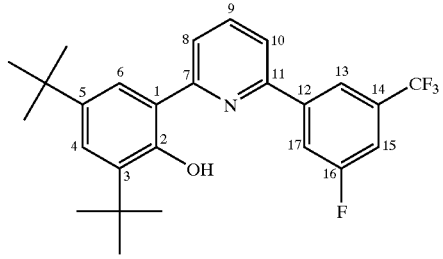

Intermediate 5

Following the procedure described above for preparing Intermediate 1, a mixture of 3,5-di-tert-butyl-2-methoxyacetophenone (2.99 g, 11.40 mmol) and potassium tert-butoxide (2.56 g, 22.80 mmol) in THF was stirred for 2 hr at room temperature under nitrogen atmosphere, and a solution of 1-N,N-dimethylamino-3-(3'-trifluoromethylphenyl)-3-oxo-1-propene (2.94 g, 11.30 mmol) in THF (30 ml) was added. The resultant mixture was stirred for 12 hr at room temperature during which time a dark red solution formed. A 2M solution of ammonium acetate in acetic acid (30 ml) was added to the solution, THF was removed by distillation over 2 hr, and the resultant mixture was added to $CH_2Cl_2$ (100 ml). The organic layer was collected, washed with water to remove excess acetic acid, neutralized with saturated sodium bicarbonate solution, and washed with brine. The organic layer was dried over anhydrous magnesium sulphate, and volatiles removed in vacuo. The resultant red oil (2.635 g) was reacted with molten pyridinium chloride (6.63 g, 57.40 mmol) under $N_2$ atmosphere at 230° C. for 12 hr as described above in Example 1. The resultant crude yellow solid was washed with cold n-pentane to afford Intermediate 4 as a yellow solid. Yield: 1.74 g, 68%.

Intermediate 5: $^1$H NMR (500 MHz, $CDCl_3$): δ 1.37 (s, 9H, 5-$^t$Bu), 1.50 (s, 9H, 3-$^t$Bu), 7.43 (d, J=8.0 Hz, 1H, H$^{15}$), 7.45 (d, J=2.4 Hz, 1H, H$^6$), 7.63 (m, 1H, H$^9$), 7.68 (d, J=2.4 Hz, 1H, H$^4$), 7.86 (d, J=9.3 Hz, 1H, H$^{17}$), 7.95 (m, 2H, H$^8$ and H$^{10}$), 7.97 (s, 1H, H$^{13}$), 14.06 (s, 1H, OH). $^{13}$C NMR (126 MHz, $CDCl_3$): δ 29.76 (3-$CMe_3$), 31.72 (5-$CMe_3$), 34.55 and 35.53 ($CMe_3$), 113.70 (dq, $^2J_{CF}$=24.8 Hz, $^3J_{CF}$=3.5 Hz, C$^{15}$), 117.52 (d, $^2J_{CF}$=22.7 Hz, C$^{17}$), 118.57 (C$^9$), 119.71 (m, $^3J_{CF}$=3.7 Hz, C$^{13}$), 120.05 and 138.89 (C$^8$ and C$^{10}$), 121.36 (C$^4$), 126.90 (C$^6$), 133.50 (m, $CF_3$), 163.23 (d, $^1J_{CF}$=250.0 Hz, C$^{16}$); 40° carbons: δ 118.07, 138.03, 140.45, 141.90, 141.96, 151.97, 156.63, 159.83. $^{19}$F NMR (376 MHz, $CDCl_3$): δ −63.29 ($CF_3$), −109.75 (F$^{16}$). FAB-MS (+ve, m/z): 445 [M$^+$].

Example 11

Example 11 describes the synthesis of Catalyst 6:

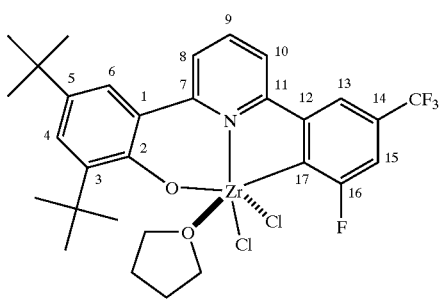

Catalyst 6

A solution of Intermediate 5 (0.200 g, 0.45 mmol) in toluene/THF (5:1) was slowly added to a stirred solution of [$Zr(CH_2Ph)_2Cl_2(OEt_2)(dioxane)_{0.5}$] (0.208 g, 0.45 mmol) in toluene/THF (5:1) at −78° C. The reaction mixture was allowed to warm to room temperature and stirred for 12 hr during which time a yellow solution formed. The solution was filtered, concentrated to ca. 10 ml and stored at −78° C. for 2–3 days to provide a crude yellow solid. The solid was isolated and recrystallized from toluene to afford Catalyst 6 as orange crystals. Yield: 0.25 g, 78%.

Catalyst 6: $^1$H NMR (600 MHz, $C_6D_6$): δ 0.83 (br, 4H, thf), 1.32 (s, 9H, 5-$^t$Bu), 1.68 (s, 9H, 3-$^t$Bu), 3.46 (br, 4H, thf), 6.84 (d, J=7.7 Hz, 1H, H$_{10}$), 6.99 (t, J=8.0 Hz, 1H, H$^9$), 7.19 (d, $^3J_{HF}$=4.0 Hz, 1H, H$^{"15}$), 7.34 (d, J=8.0 Hz, 1H, H$^8$), 7.48 (d, J=2.3 Hz, 1H, H$^6$), 7.56 (s, 1H, H$^{13}$), 7.68 (d, J=2.3 Hz, 1H, H$^4$). $^{13}$C NMR (151 MHz, $C_6D_6$): δ 25.33 (thf), 30.68 (3-$CMe_3$), 32.02 (5-$CMe_3$), 35.06 and 36.05 ($CMe_3$), 73.87 (thf), 113.55 (dq, $^2J_{CF}$=31.9 Hz, $^3J_{CF}$=3.6 Hz, C$^{15}$), 117.15 (q, $^3J_{CF}$=3.3 Hz, C$^{13}$), 118.36 (C$^{10}$), 124.22 (C$^8$), 125.06 (C$^6$), 127.98 (C$^4$), 133.08 (m, $CF_3$), 141.17 (C$^9$), 147.68 (d, $J_{CF}$=21.4 Hz, C$^{16}$); 4° carbons, 138.71, 144.07, 155.45, 158.87, 162.52, 166.33, 167.89, 170.04, 170.46. $^{19}$F NMR (376 MHz, $C_6D_6$): −62.37 ($CF_3$), −84.01 (F$^{16}$). Anal. Calcd. (%) For $C_{30}H_{33}F_4NO_2ZrCl_2$ (679.126): C, 53.17; H, 4.91; N, 2.07. Found: C, 49.43; H, 4.89; N, 2.03.

Example 12

Example 12 describes the reaction of Catalyst 3 with the activator tris(pentafluorophenyl)boron, $B(C_6F_5)_3$.

Figure 8:
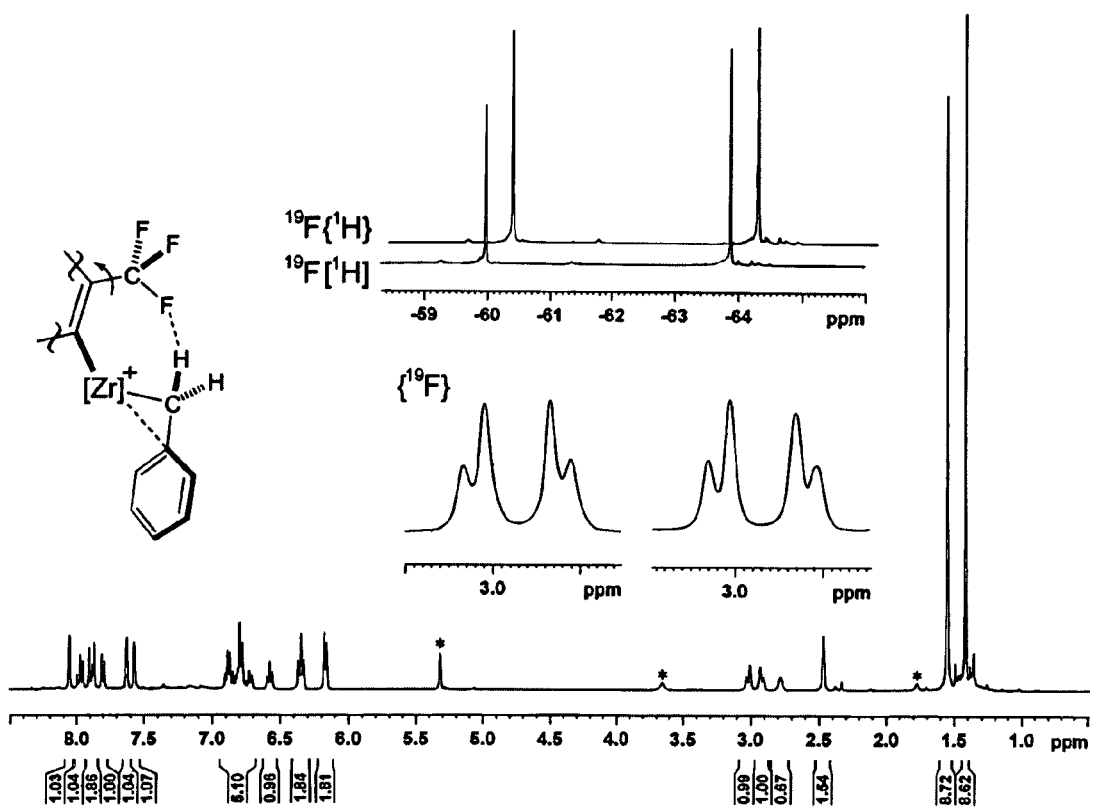
FIG. 8 shows the $^1$H (400 MHz) and $^{19}$F (376 MHz, $CF_3$ region, ppm axis displaced for clarity) NMR spectra ($CD_2Cl_2$+$d_8$-THF, 300 K) for $\eta^2$—$CH_2$Ph cation derived from reaction of Catalyst 3 with $B(C_6F_5)_3$, demonstrating effects of $^{19}$F- and $^1$H-decoupling respectively (*=deuterated solvents).

Catalyst 3 was reacted with 1 equivalent of $B(C_6F_5)_3$ in $CD_2Cl_2$ and $d_8$-THF in an NMR tube. As shown in FIG. 8, the broad upfield $^1$H doublet peak for one of the methylene protons and the downfield $^{19}$F resonance for the proximal $CF_3$ group are both partially sharpened upon decoupling of the $^{19}$F and $^1$H nuclei respectively. It is noted that the $^{13}C\{^1H\}$ NMR spectrum (400 MHz) contains a slightly broad but resolved quartet signal at 76.9 ppm ($^{2h}J_{CF}$=4 Hz) for the $ZrCH_2$ group. The NMR spectrum indicated formation of a η$^2$-benzyl cation that is presumably stabilized by the $d_8$-THF ligand.

Example 13

Example 13 describes the results of ethylene polymerization using Catalyst 1 as catalyst and MAO as activator.

The ethylene polymerization was performed under 1 atm ethylene overpressure in toluene in a 100 mL glass reactor equipped with a magnetic stir bar. Catalyst 1 (5.8 mg, 9.19 μmol) and toluene (20 mL) were added to the reactor and stirred to form a solution. The reactor was submerged in a liquid bath at 23° C. for 30 minutes, and a toluene solution of methylaluminoxane (MAO) (9.19 mmol, 1000 equivalents) was added. Polymerization was initiated by purging with ethylene gas for 5 minutes, and the reactor was maintained under 1 atmosphere (atm) of ethylene for 10 minutes at 23° C. The ethylene gas feed was stopped, and the polymerization was terminated by addition of HCl-acidified methanol (40 mL). The resultant solid polymer was collected by filtration, washed with acidified methanol and dried in vacuum at 60° C. for 12 h to afford 0.013 g of polymer. Melting point: 128° C. The calculated activity of Catalyst 1 was 11.7 g mmol$^{-1}$ h$^{-1}$ atm$^{-1}$.

Example 14

Ethylene polymerization was performed as described above in Example 13 using Catalyst 3 (5.3 mg, 6.91 μmol) and MAO (6.91 mmol; 1000 equivalents) for 10 min at 23° C. to afford 0.130 g of polymer. Melting point: 131° C. The calculated activity of Catalyst 3 was 113 g mmol$^{-1}$ h$^{-1}$ atm$^{-1}$.

Example 15

Ethylene polymerization was performed as described above in Example 13 using Catalyst 3 (7.2 mg, 9.39 μmol) and MAO (9.39 mmol; 1000 equivalents) for 10 min at −3°

C. to afford 0.403 g of polymer. Melting point: 130° C. The calculated activity of Catalyst 3 was 258 g mmol$^{-1}$ h$^{-1}$ atm$^{-1}$.

Example 16

Ethylene polymerization was performed as described above in Example 13 using Catalyst 3 (5.5 mg, 7.17 µmol) and MAO (7.17 mmol; 1000 equivalents) for 10 min at 50° C. to afford 0.130 g of polymer. Melting point: 132° C. The calculated activity of Catalyst 3 was 109 g mmol$^{-1}$ h$^{-1}$ atm$^{-1}$.

Example 17

Ethylene polymerization was performed as described above in Example 13 using Catalyst 3 (5.3 mg, 6.91 µmol) and MAO (13.8 mmol; 2000 equivalents) for 10 min at 23° C. to afford 0.914 g of polymer. Melting point: 131° C. The calculated activity of Catalyst 3 was 793 g mmol$^{-1}$ h$^{-1}$ atm$^{-1}$.

Example 18

Ethylene polymerization was performed as described above in Example 13 using Catalyst 5 (4.7 mg, 6.72 µmol) and MAO (6.72 mmol; 1000 equivalents) for 10 min at 23° C. to afford 0.006 g of polymer. The calculated activity of Catalyst 5 was 4 g mmol$^{-1}$ h$^{-1}$ atm$^{-1}$.

Example 19

Ethylene polymerization was performed as described above in Example 13 using Catalyst 6 (7.1 mg, 10.31 [mol) and MAO (10.31 mmol; 1000 equivalents) for 10 min at 23° C. to afford 1.022 g of polymer. Melting point: 125° C. The calculated activity of Catalyst 7 was 595 g mmol mmol$^{-1}$ h$^{-1}$ atm$^{-1}$.

Example 20

Ethylene polymerization was performed as described above in Example 13 using Catalyst 4 (5.2 mg, 7.18 µmol) and MAO (7.18 mmol; 1000 equivalents) for 2 min at 24° C. to afford 0.396 g of polymer. Melting point: 134° C. The calculated activity of Catalyst 4 was 1654 g mmol mmol$^{-1}$ h$^{-1}$ atm$^{-1}$.

Example 21

Ethylene polymerization was performed as described above in Example 13 using Catalyst 4 (5.4 mg, 7.46 µmol) and MAO (7.46 mmol; 1000 equivalents) for 2 min at 0° C. to afford 0.434 g of polymer. Melting point: 136° C. The calculated activity of Catalyst 4 was 1744 g mmol mmol$^{-1}$ h$^{-1}$ atm$^{-1}$.

Example 22

Ethylene polymerization was performed as described above in Example 13 using Catalyst 4 (5.0 mg, 6.91 µmol) and MAO (6.91 mmol; 1000 equivalents) for 2 min at 50° C. to afford 0.209 g of polymer. Melting point: 133° C. The calculated activity of Catalyst 4 was 907 g mmol mmol$^{-1}$ h$^{-1}$ atm$^{-1}$.

Example 23

Example 23 describes the results of 1-hexene polymerization using a catalyst prepared from Catalyst 1 and MAO.

Polymerization of 1-hexene was performed at 1 atm. pressure in toluene in a 100 mL glass reactor equipped with a magnetic stir bar. Catalyst 1 (5.0 mg, 7.92 µmol) and toluene (20 mL) were added to the reactor and stirred to form a solution. A toluene solution of methylaluminoxane (MAO) (7.92 mmol; 1000 equivalents) was added to the reactor and the contents stirred. The reactor was submerged in a liquid bath at 23° C. for 10 minutes, neat 1-hexene (5 mL) was added to the reactor, and the polymerization was performed for 5 hr The polymerization was then terminated by addition of HCl-acidified methanol (40 mL). The resultant polymer was extracted with $CH_2Cl_2$, precipitated with methanol, and dried in vacuum for 12 hr to afford 0.246 g of polymer. The calculated activity of Catalyst 1 was 6.2 g mmol$^{-1}$ h$^{-1}$.

Example 24

1-Hexene polymerization was performed as described above in Example 23 using Catalyst 3 (5.5 mg, 7.17 µmol) and MAO (7.92 mmol; 1000 equivalents) for 5 hr at 23° C. to afford 0.387 g of polymer. The calculated activity of Catalyst 3 was 10.8 g mmol$^{-1}$ h$^{-1}$.

Example 25

1-Hexene polymerization was performed as described above in Example 23 using Catalyst 3 (6.7 mg, 8.74 µmol) and MAO (8.74 mmol; 1000 equivalents) for 5 hr at 0° C. to afford 0.119 g of polymer. The calculated activity of Catalyst 3 was 2.7 g mmol$^{-1}$ h$^{-1.}$ As is apparent from the previous general description and the specific embodiments, while forms of the invention have been illustrated and described, various modifications can be made without departing from the scope and spirit of the invention. Accordingly, it is not intended that the invention be limited thereby.

A number of references have been cited and the entire disclosures of which are incorporated herein by reference.

What is claimed is:

1. An olefin polymerization catalyst system prepared from a catalyst and an activator, wherein the catalyst is of formula:

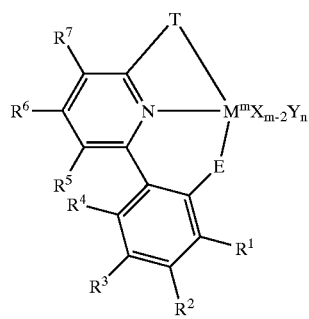

wherein:

R$^1$–R$^7$ are each independently —H, -halo, —NO$_2$, —CN, —(C$_1$–C$_{30}$)hydrocarbyl, —O(C$_1$–C$_{30}$)hydrocarbyl, —N((C$_1$–C$_{30}$)hydrocarbyl)$_2$, —Si((C$_1$–C$_{30}$)hydrocarbyl)$_3$, —(C$_1$–C$_{30}$)heterohydrocarbyl, -aryl, or -heteroaryl, each of which is unsubstituted or substituted with one or more —R$^8$ groups; or two R$^1$–R$^7$ are joined to form a cyclic group;

R$^8$ is -halo, —(C$_1$–C$_{30}$)hydrocarbyl, —O(C$_1$–C$_{30}$)hydrocarbyl, —NO$_2$, —CN, —Si((C$_1$–C$_{30}$)hydrocarbyl)$_3$, —N((C$_1$–C$_{30}$)hydrocarbyl)$_2$, —(C$_1$–C$_{30}$)heterohydrocarbyl, -aryl, or -heteroaryl;

T is —CR$^9$R$^{10}$— wherein R$^9$ and R$^{10}$ are defined as for R$^1$ above;

E is a Group 16 element;

M is a metal selected from the group consisting of metallic Group 3–6 elements;

m is the oxidation state of M;

X is R$^1$ excluding —H, wherein X is bonded to M;

Y is a neutral ligand datively bound to M; and n is an integer ranging from 0 to 5.

2. The olefin polymerization catalyst of claim 1, wherein the activator is selected from the group consisting of trimethylaluminum, triethylaluminum, tri-isobutylaluminum, tri-n-octylaluminum, methylaluminum dichloride, ethylaluminum dichloride, dimethylaluminum chloride, diethylaluminum chloride, aluminoxanes, dimethylphenylammonium tetra(pentafluorophenyl)borate, trityl tetra(pentafluorophenyl)borate, tris(pentafluorophenyl)boron, tris(pentabromophenyl)boron, and mixtures thereof.

3. The olefin polymerization catalyst system of claim 1, wherein M is titanium, zirconium or hafnium.

4. The olefin polymerization catalyst system of claim 1, wherein X is halide, unsubstituted —C$_1$–C$_{30}$)hydrocarbyl or substituted —(C$_1$–C$_{30}$)hydrocarbyl.

5. The olefin polymerization catalyst system of claim 1, wherein X is benzyl.

6. The olefin polymerization catalyst system of claim 1, wherein E is —O—.

7. The olefin polymerization catalyst system of claim 1, wherein at least one of R$^1$–R$^7$ and R$^9$–R$^{10}$ is selected from the group consisting of —C(halide)$_3$, CH(halide)$_2$ and —CH$_2$(halide).

8. A method for polymerizing an olefin comprising contacting an olefin with the olefin polymerization catalyst system of claim 1.

9. The method of claim 8, wherein the olefin is ethylene, propylene, 1-butene, 2-pentene, 1-hexene, 1-octene, styrene, 1,3-butadiene, norbornene, each of which may be substituted or unsubstituted, or mixtures thereof.

10. The method of claim 9, wherein the olefin is ethylene or 1-hexene.

11. The method of claim 8, wherein at least one of R$^1$–R$^7$ and R$^9$–R$^{10}$ is selected from the group consisting of —C(halide)$_3$, CH(halide)$_2$ and —CH$_2$(halide).

12. An olefin polymerization catalyst system prepared from a catalyst and an activator, wherein the catalyst is of formula:

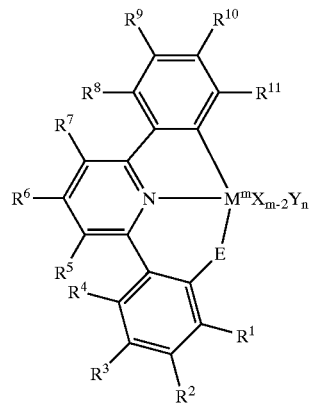

wherein:

R$^1$–R$^{11}$ are each independently —H, -halo, —NO$_2$, —CN, —(C$_1$–C$_{30}$)hydrocarbyl, —O(C$_1$–C$_{30}$)hydrocarbyl, —N((C$_1$–C$_{30}$)hydrocarbyl)$_2$, —Si((C$_1$–C$_{30}$)hydrocarbyl)$_3$, —(C$_1$–C$_{30}$)heterohydrocarbyl, -aryl, -heteroaryl, each of which is unsubstituted or substituted with one or more —R$^{12}$ groups; or two R$^1$–R$^7$ are joined to form a cyclic group;

each R$^{12}$ is independently -halo, —NO$_2$, —CN, —(C$_1$–C$_{30}$)hydrocarbyl, —O(C$_1$–C$_{30}$)hydrocarbyl, —N((C$_1$–C$_{30}$)hydrocarbyl)$_2$, —Si((C$_1$–C$_{30}$)hydrocarbyl)$_3$, —(C$_1$–C$_{30}$)heterohydrocarbyl, -aryl, or -heteroaryl;

E is a Group 16 element;

M is a metal selected from the group consisting of metallic Group 3–Group 6 elements;

m is the oxidation state of M;

X is R$^1$ excluding —H, wherein X is bonded to M;

Y is a neutral ligand datively bound to M; and n is an integer ranging from 0 to 5.

13. The olefin polymerization catalyst system of claim 12, wherein the activator is selected from the group consisting of trimethylaluminum, triethylaluminum, tri-isobutylaluminum, tri-n-octylaluminum, methylaluminum dichloride, ethylaluminum dichloride, dimethylaluminum chloride, diethylaluminum chloride, aluminoxanes, dimethylphenylammonium tetra(pentafluorophenyl)borate, trityl tetra(pentafluorophenyl)borate, tris(pentafluorophenyl)boron, tris(pentabromophenyl)boron, and mixtures thereof.

14. The olefin polymerization catalyst system of claim 12, wherein M is titanium, zirconium or hafnium.

15. The olefin polymerization catalyst system of claim 12, wherein M is Ti or Zr; E is —O—; m is 4; n is 0 or 1; and X is halo, —(C$_1$–C$_{30}$)hydrocarbyl or benzyl.

16. The olefin polymerization catalyst system of claim 12, wherein R$^{11}$ is —CF$_3$.

17. The olefin polymerization catalyst system of claim 12, wherein M is Zr; R$^1$ and R$^3$ are —C(CH$_3$)$_3$; R$^2$ and R$^4$–R$^{11}$ are —H; X is —CH$_2$(C$_6$H$_5$); and n is 0.

18. The olefin polymerization catalyst system of claim 12, wherein M is Zr; R$^1$ and R$^3$ are —C(CH$_3$)$_3$; R$^2$ and R$^4$–R$^{11}$ are —H; X is —Cl; n is 1; and Y is -tetrahydrofuran.

19. The olefin polymerization catalyst system of claim 12, wherein M is Zr; R$^1$ and R$^3$ are —C(CH$_3$)$_3$; R$^9$ and R$^{11}$ are —CF$_3$; R$^2$, R$^4$–R$^8$ and R$^{10}$ are —H; X is —CH$_2$(C$_6$H$_5$); and n is 0.

20. The olefin polymerization catalyst system of claim 12, wherein M is Ti; $R^1$ and $R^3$ are —$C(CH_3)_3$; $R^9$ and $R^{11}$ are —$CF_3$; $R^2$, $R^4$–$R^8$ and $R^{10}$ are —H; X is —$CH_2(C_6H_5)$; and n is 0.

21. The olefin polymerization catalyst system of claim 12, wherein M is Zr; $R^1$ and $R^3$ are —$C(CH_3)_3$; $R^9$ is —$CF_3$; $R^2$, $R^4$–$R^8$ and $R^{10}$–$R^{11}$ are —H; X is —$CH_2(C_6H_5)$; and n is 0.

22. The olefin polymerization catalyst system of claim 12, wherein M is Zr; $R^1$ and $R^3$ are —$C(CH_3)_3$; $R^9$ is —$CF_3$; $R^{11}$ is —F; $R^2$, $R^4$–$R^8$ and $R^{10}$ are —H; X is —Cl; n is 1; and Y is tetrahydrofuran.

23. The olefin polymerization catalyst system of claim 12, wherein at least one of $R^1$–$R^{11}$ is selected from the group consisting of —$C(halide)_3$, $CH(halide)_2$ and —$CH_2(halide)$.

24. A method for polymerizing an olefin comprising contacting an olefin with the olefin polymerization catalyst system of claim 12.

25. The method of claim 24, wherein the olefin is ethylene, propylene, 1-butene, 2-pentene, 1-hexene, 1-octene, styrene, 1,3-butadiene, norbornene, each of which may be substituted or unsubstituted, or mixtures thereof.

26. The method of claim 25, wherein the olefin is ethylene or 1-hexene.

27. The method of claim 24, wherein at least one of $R^1$–$R^{11}$ is selected from the group consisting of —$C(halide)_3$, $CH(halide)_2$ and —$CH_2(halide)$.

* * * * *